(12) United States Patent
Gao et al.

(10) Patent No.: US 10,895,560 B2
(45) Date of Patent: Jan. 19, 2021

(54) ELECTRONIC NOSE INSTRUMENT FOR SENSORY QUALITY EVALUATION OF TOBACCO AND TOBACCO PRODUCT

(71) Applicant: EAST CHINA UNIVERSITY OF SCIENCE AND TECHNOLOGY, Shanghai (CN)

(72) Inventors: Daqi Gao, Shanghai (CN); Zejian Wang, Shanghai (CN); Xiaoqin Zhang, Shanghai (CN); Jiamin Song, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 16/651,722

(22) PCT Filed: Mar. 18, 2018

(86) PCT No.: PCT/CN2018/079389
§ 371 (c)(1),
(2) Date: Mar. 27, 2020

(87) PCT Pub. No.: WO2019/085369
PCT Pub. Date: May 9, 2019

(65) Prior Publication Data
US 2020/0256837 A1    Aug. 13, 2020

(30) Foreign Application Priority Data

Oct. 31, 2017 (CN) ........................ 2017 1 1054914
Oct. 31, 2017 (CN) ........................ 2017 1 1060781

(51) Int. Cl.
*G01N 33/00* (2006.01)
*G01N 1/24* (2006.01)
*G06N 3/08* (2006.01)

(52) U.S. Cl.
CPC ........... *G01N 33/0001* (2013.01); *G01N 1/24* (2013.01); *G01N 33/0006* (2013.01);
(Continued)

(58) Field of Classification Search
CPC ........... G01N 33/0001; G01N 33/0006; G01N 33/0031; G01N 33/0036; G01N 33/0098; G01N 1/24; G06N 3/08
See application file for complete search history.

(56) References Cited

U.S. PATENT DOCUMENTS 6,450,008 B1 *   9/2002   Sunshine ............... B82Y 15/00
                                                        702/27
7,531,137 B2     5/2009   Uluyol
2019/0302069 A1 * 10/2019 Francisco Swenson Pontes .........
                                                    G01N 33/0098

FOREIGN PATENT DOCUMENTS

CN          1115112 C    *  7/2003
CN          101101299       1/2008
(Continued)

OTHER PUBLICATIONS

International Search Report issued in PCT/CN2018/079389 dated Jun. 27, 2018.

*Primary Examiner* — Mohamed Charioui
(74) *Attorney, Agent, or Firm* — Workman Nydegger

(57) ABSTRACT

Provided is a sensory quality evaluation method for tobacco and tobacco products using an electronic nose instrument. The electronic nose instrument includes a gas sensor array module, an automatic smoke sampling system, a computer control and data analysis system, and an automatic ignition device. These components are integrated in a test box to make the instrument be structure miniaturization and work automation. The large tobacco data is established, in which the relationship between the responses of gas sensor array and the brand labels and sensory quality index scores by (Continued)

testing a large number of standard cigarette samples. A cascade type of modular neural networks is proposed with revised activation function and new decision-making and quantification rules to simulate the smoking and evaluating process of the professional panel. The electronic nose instrument and method realize on-site detection, discrimination and quality score estimation of a large number of tobacco and tobacco products.

14 Claims, 12 Drawing Sheets

(52) U.S. Cl.
CPC ..... *G01N 33/0031* (2013.01); *G01N 33/0036* (2013.01); *G01N 33/0098* (2013.01); *G06N 3/08* (2013.01)

(56) References Cited

FOREIGN PATENT DOCUMENTS

| | | |
|---|---|---|
| CN | 103336090 | 10/2013 |
| CN | 105699437 | 6/2016 |
| CN | 107807199 | 3/2018 |

* cited by examiner

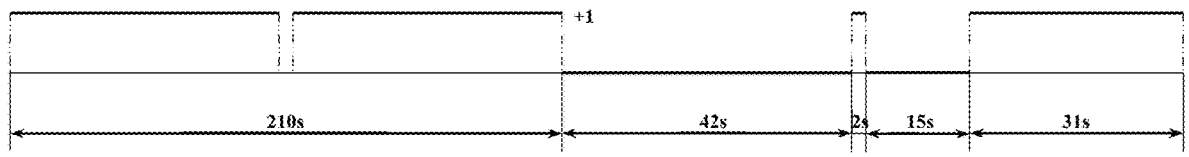

(a) Change of on-off states of first two-position two-port electromagnetic valve (II-1)

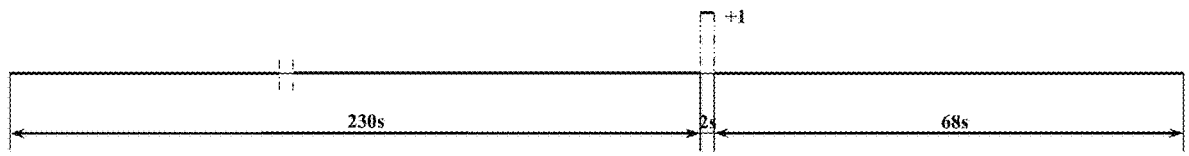

(b) Change of on-off states of second two-position two-port electromagnetic valve (II-2)

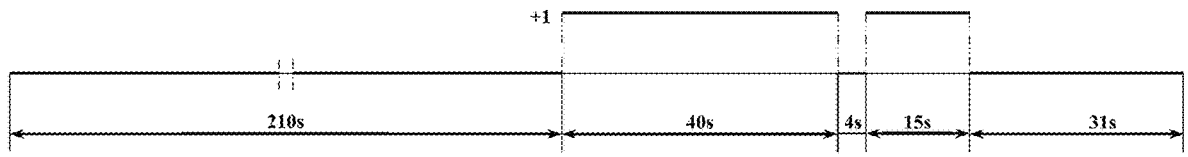

(c) Change of on-off states of third two-position two-port electromagnetic valve (II-3)

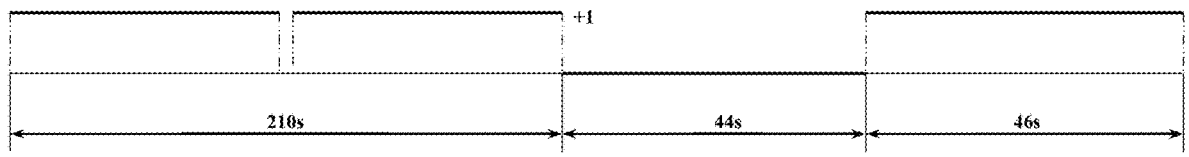

(d) Change of on-off states of fourth two-position two-port electromagnetic valve (II-4)

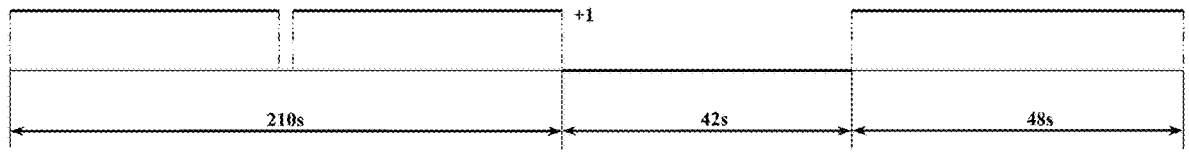

(e) Change of on-off states of fifth two-position two-port electromagnetic valve (II-5)

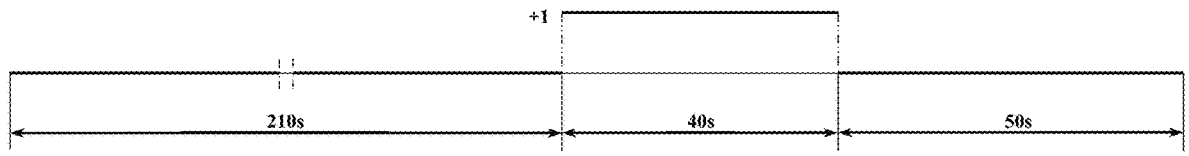

(f) Change of on-off states of sixth two-position two-port electromagnetic valve (II-6)

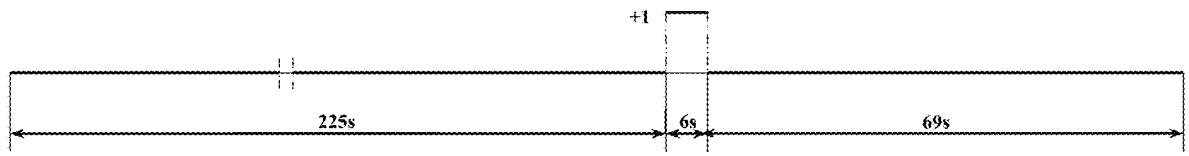

(g) Change of on-off states of ignition coil (IV-1)

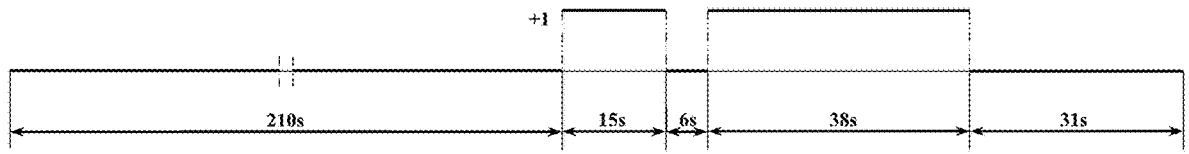

(h) Change of on-off states of electromagnetic coil (IV-4)

Fig. 11

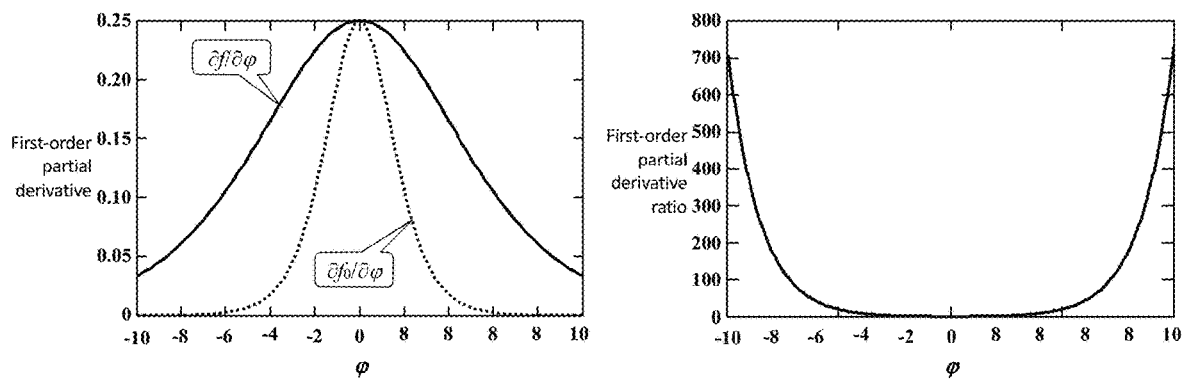

(a), Curves of two first-order partial derivatives, $\partial f/\partial \varphi$ and $\partial f_0/\partial \varphi$, for the modified and standard Sigmoid activation functions in $\varphi \in [-10, 10]$.

(b), Ratio curve of two first-order partial derivatives, $\partial f/\partial \varphi : \partial f_0/\partial \varphi$, for the modified and standard Sigmoid activation functions in $\varphi \in [-10, 10]$.

Fig. 15

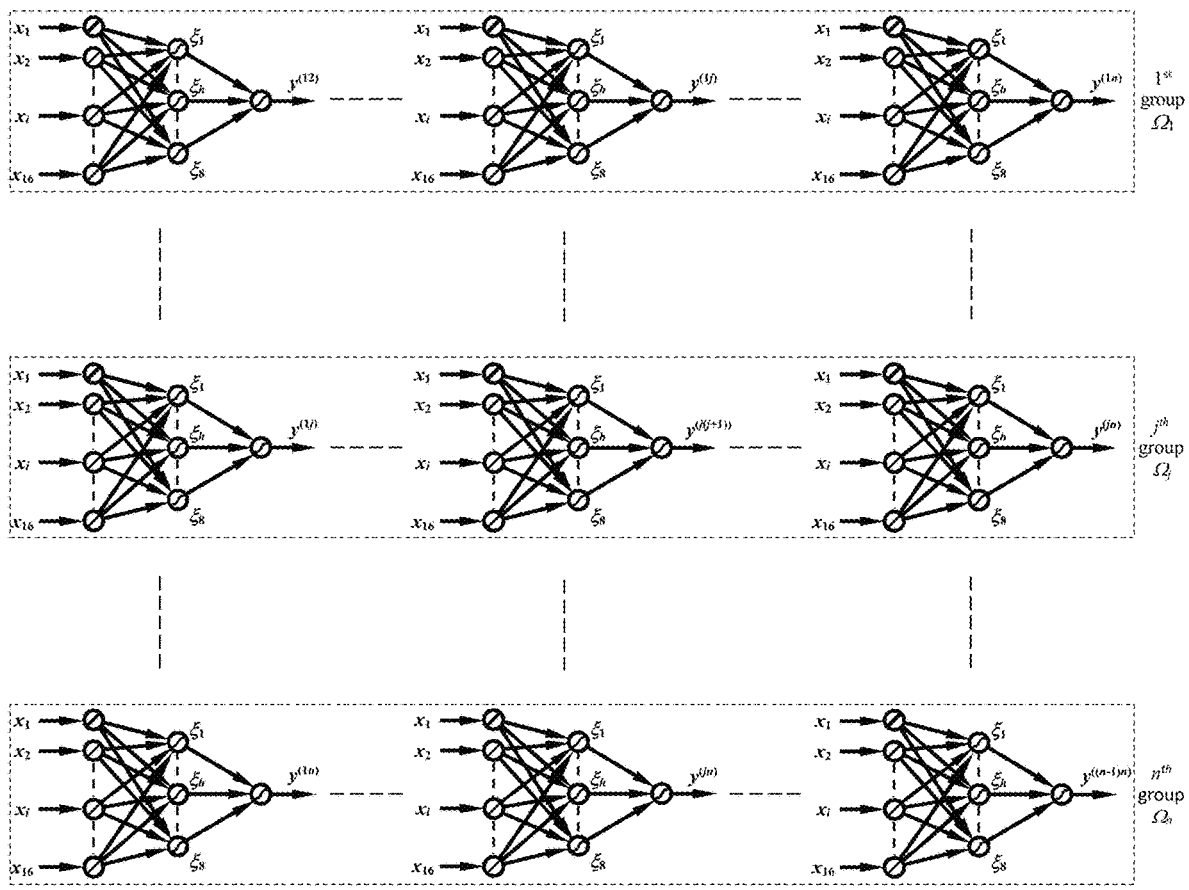

Fig. 16

ELECTRONIC NOSE INSTRUMENT FOR SENSORY QUALITY EVALUATION OF TOBACCO AND TOBACCO PRODUCT

CROSS-REFERENCE TO RELATED APPLICATIONS

This application is a United States national phase application of co-pending international patent application number PCT/CN2018/079389, titled "Electronic Nose Instrument and Sensory Quality Evaluation Method for Tobacco and Tobacco Product" and filed Mar. 18, 2018, which claims the benefit of and priority to China patent application No. 201711054914.6 titled "Electronic Nose Instrument and Sensory Quality Detection Method for Tobacco and Tobacco Products" and filed Oct. 31, 2017, and to China patent application No. 201711060781.3 titled "Sensory Quality Evaluation Method for Tobacco and Tobacco Products Using Electronic Nose Instrument" and filed Oct. 31, 2017, disclosures of all of which are incorporated herein by reference in their entireties.

TECHNICAL FIELD

The present disclosure is directed to a sensory quality evaluation method for tobacco and tobacco products using an electronic nose instrument. In particular, the method of the present disclosure relates to the fields of computer, precision measurement, precision machinery, automatic control, analytical chemistry, and tobacco. The present disclosure aims at the quality control and market supervision of tobacco and tobacco products, and mainly solves the problems of automation, integration, miniaturization of electronic nose instruments; on-site detection, recognition and sensory quality index estimation of tobacco and tobacco products. For the sake of simplicity, the phrase "electronic nose instrument" is also called "tobacco electronic nose instrument" hereinafter.

BACKGROUND

"Sensory smoking" refers to the sensory recognition of qualities and effects of tobacco, tobacco products and tobacco flavors by using specific organs such as oral cavity, nasal cavity and larynx, namely the evaluation of internal or sensory qualities of cigarettes, in a specific environment. At present, the quality evaluation of tobacco and tobacco products depends entirely on the human senses, and is determined by human sensory smoking. Compared with other flavor substances, such as wine, tea, food, etc., tobacco and tobacco products are unique in that their quality index evaluation depends entirely on human senses, and so far there is no practically feasible physical and chemical detection and analysis method.

The China industry standard in force "Tobacco and Tobacco Products—Sensory Evaluation Method" (YC/T138-1998) was issued by the State Tobacco Monopoly Administration of China on Mar. 12, 1998 and implemented on May 1, 1998. The industry standard is widely used in production of tobacco enterprises and market management of tobacco industry. According to the industry standard, a cigarette assessor evaluates a tobacco and tobacco product sample by the overall circulation smoking manner, and fills the sensory quality index scores shown in Table 1. In Table 1, the unit of gloss and harmony index scores is 0.5, while the unit of aroma, impurity, irritation and aftertaste index scores is 1.0. According to the percentage system, the sum of full scores of aroma and impurity gas reaches 52 points, accounting for 52%.

Except for the single external quality index of color, the five internal quality indices of aroma, harmony, impurity, irritation, and aftertaste shown in Table 1 are directly or indirectly related to olfactory sensation, where the value in each parentheses represents a full score. In order to make the sensory evaluation results as objective, fair and accurate as possible, an evaluator or cigarette assessor must undergo professional theoretical training and technical exercise, maintain the correct psychological state and good physical condition; furthermore, the evaluation environment condition should meet the standard requirement, and the tested cigarette samples should be calibrated and unified before evaluation. There should be enough assessors in the smoking panel, usually 7 or more. The average score given by all assessors in the panel is the final sensory quality index score of a cigarette sample, and the significance test is carried out with binomial distribution and $\chi^2$ distribution.

TABLE 1

Primary record for sensory quality inspection of cigarettes (tobacco products) (YC/T 138-1998)*

| Item Score segment | Color (6) | | | Aroma (36) | | | Harmony (6) | | | Impurity (16) | | | Irritation (16) | | | Aftertaste (20) | | | |
|---|---|---|---|---|---|---|---|---|---|---|---|---|---|---|---|---|---|---|---|
| | A | B | C | A | B | C | A | B | C | A | B | C | A | B | C | A | B | C | |
| Sample number | Brand number | | | | | | | | | | | | | | | | | | |
| | 6 | 4 | 2 | 36 | 28 | 18 | 6 | 4 | 2 | 16 | 12 | 9 | 16 | 13 | 11 | 20 | 14 | 8 | Sum |
| . . . | | | | | | | | | | | | | | | | | | | |

According to the industry standard YC/T138, the sensory assessors of tobacco and tobacco products are divided into three categories: primary assessors, selected assessors and experts. After special selection and training, the basic conditions that assessors should satisfy are: (a) having professional knowledge of tobacco and tobacco products; (b) having interest and experience in sensory evaluation; (c) being healthy without any sensory deficiencies; (d) having normal personal sensitivity and mutual sensitivity; (e) having normal physiological status during sensory smoking; (f) not eating spicy and other irritant foods and not drinking wines before evaluation; (g) no obvious body odor and not using odorous cosmetics. In order to prevent sensory fatigue and discomfort, the number of cigarette samples continuously evaluated by a single assessor should generally be controlled within 25 pieces per day. The evaluation process should be carried out in a quiet, interference-free, ventilated and odorless room.

At present, "Sensory smoking" is not only the only feasible method to determine the quality of tobacco and tobacco products, but also the basis to determine their formulation structures. "Sensory smoking" is a necessary and decisive means to develop new products and maintain the inherent style and quality stability of existing products. For consumers, i.e., smokers, smoking is a kind of physiological stimulation and good enjoyment, and there is no labor problem; for assessors, sensory smoking is a very hard and meticulous work. In the sensory smoking process, one assessor/expert should be highly concentrated in mind, and makes judgments in a few minutes.

It is a global common consensus that smoking is harmful for human health. After decades of long and tedious process of component analysis, the tobacco academia had finally found that cigarette smoke gas is a complex aerosol composed of 4,000-5,000 components. During smoking, most of the smoke is inhaled into the lung, and the harmful substances either stay in the lung, or enter the digestive tract, or enter the blood circulation and flow through the whole body. Scientific research has pointed out that nicotine is the main cause of smoking addiction and has a certain toxic effect on the human body, especially on the cardiovascular system. Tar contains cancer inducers and promoters, such as benzopyrene. Moreover, phenols, alcohols, acids, aldehydes, CO, HCN, $NH_3$ and other substances in cigarette smoke gases are toxic and carcinogenic. In short, if smoking for a long time, the carcinogens and carcinogens in smoke gases will damage the normal cells and greatly increase the risk of lung cancer and other diseases. Therefore, a long-term smoking of tobacco and tobacco products will undoubtedly cause serious harm to the health of smokers.

According to the current industry standard YC/T138, the estimation of internal sensory quality of cigarettes generally adopts the "overall circulation smoking manner": an assessor inhales the tested smoke gas into the mouth, swallows through the throat, slowly exhales from the nasal cavity, and uses all the sensory organs to evaluate the inhaled smoke gas. Because of the difference of sensitivities of sensory organs and the influence on the captures of various indicators, physiological and psychological condition, environmental condition and other factors, there are differences in the description and judgment of the evaluation results among the cigarette assessors, which fully illustrates the limitation of the sensory evaluation methods.

TABLE 2

Sensory evaluation indicators for in-process tobacco products (YC/T415-2011)

Enterprise: _____ Procedure or processing section: _____

| No. | Aroma characteristics | | | | Smoke characteristics | | | | Taste characteristics | | |
|---|---|---|---|---|---|---|---|---|---|---|---|
| | Quality | Quantity | Penetration | Impurity | Concentration | Strength | Delicacy | Clustering | Irritation | Dryness | Cleanliness |
| 1 | | | | | | | | | | | |
| 2 | | | | | | | | | | | |
| ... | | | | | | | | | | | |

Grade, module or brand: _____

| Enterprise: No. | Procedure or processing section: | | | | Judgment of processing result | | | | | |
|---|---|---|---|---|---|---|---|---|---|---|
| | Taste characteristics | Aroma style | | | Change direction | | | Processing degree | | |
| | Sweet feeling | Basic consistence | Slight difference | Notable difference | Better | The same | Worse | Undue | Moderate | Inadequate |
| 1 | | | | | | | | | | |
| 2 | | | | | | | | | | |
| ... | | | | | | | | | | |

If the industry standard YC/T138 is mainly concerned with the sensory quality of tobacco products or cigarette commodities, then the main purpose of the China industry standard "Tobacco in processing—Sensory evaluation methods" YC/T415-2011 is to optimize the procedure setting and equipment technology parameters, and to control the quality of tobacco products. The standard YC/T415 divides the sensory evaluation indices into three major categories: aroma, smoke and taste, and then subdivides each category into four single items with totally 3×4=12 items, as shown in Table 2. Each index has 9 integer scores ranging from 1 to 9. The change degree of aroma style depends on the change of aroma, smoke and taste.

The main purpose of the industry standard YC/T415 is to investigate the effects of process and section changes or process parameter changes on the sensory quality and the fluctuation of tobacco products in process. The standard YC/T415 adopts the comparative evaluation method. The samples produced before or after the change of working procedure or section are taken as the control groups to evaluate their qualities after the change, i.e., the change degree of aroma style and the treatment status of working section. The results of many industrial applications have shown that the evaluation indices in the industry standard YC/T415 could comprehensively reflect the styles and quality characteristics of tobacco leaves. At present, most domestic cigarette enterprises use the standard for quality evaluation of raw materials, development of new products, substitution of cigarette formulas, and quality inspection of tobacco in manufacturing, etc.

The China industry standard "Flue-cured tobacco—Sensory evaluation methods for quality and style characteristics of tobacco leaves" YC/T530-2015 focuses on the evaluation of quality style characteristics of flue-cured tobacco leaves according to the quality requirement of Chinese-style cigarettes. The standard follows the relevant evaluation indicators of the industry standard YC/T415 and "Cigarette The sensory evaluation methods for Chinese-stylistic features" YC/T497-2014, and does the detailed classification of style and quality characteristics by combining with the quality characteristics of flue-cured tobacco leaves. Compared with the standard YC/T415, the standard YC/T530 classifies the cleanliness and sweetness indicators as the "aftertaste" category, puts forward 16 kinds of aroma, 3 kinds of aroma states and 9 kinds of impurity types, increases the softness and roundness evaluation indicators, retains aroma quality, aroma quantity, permeability, strength, concentration, impurity, irritation, dryness and softness indicators, and tries to more comprehensively reflect the style characteristics of tobacco leaves.

The three current tobacco industry standards of YC/T497, YC/T415 and YC/T138 put main focus on the quality evaluation of tobacco leaves, in-process and final products. They both rely on human senses and emphasize human senses and experiences. The intrinsic sensory quality indices, such as aroma, harmony, impurity, irritation, aftertaste, strength and penetration, are directly or indirectly related to the sense of smell.

It must be pointed out that the above-mentioned three industry standards do not regulate the specific evaluation process of assessors. Sensory smoking is the process of inhaling in the mouth, swallowing in the throat and exhaling from the nasal cavity, which is called "inhaling", "swallowing" and "exhaling". The specified sensory smoking stages are as follows:

(1), a cigarette ignition stage. A unified fire source is used;
(2), a first smoke puff stage. The first smoke gas is inhaled into the mouth with appropriate volume, and then is exhaled immediately;
(3), a smoldering combustion stage. Cigarettes burn by themselves in the ambient air;
(4), a second smoke puff stage. The second smoke gas is inhaled into the mouth with appropriate volume, stayed in the mouth for 2-4 s, swallowed, and then the assessor closes his/her mouth lips, forcing the smoke to exhale slowly from the nasal cavity.

A large number of experiments show that the first smoke gas cannot be used as the basis for judging, because the first smoke gas is very susceptible to many factors including the smell of fire source, tobacco flavors, initial combustion state and others. "Smoking volume" is an important factor affecting the accuracy of sensory smoking. Unlike any machine, the assessors can only try to control and maintain the same volume of smoke gases between a single or between few members. According to the China national standard "Routine Analytical Cigarette-Smoking machine—Definition and standard conditions" GB/T16450-2004, the average volume of smoke gas for an assessor is 35 ml, the smoke flow rate is 17.5 ml/s, and the smoking duration is 2 s. These data are the main basis of the present disclosure.

Olfaction is a complex sensation produced by odor molecules stimulating the nasal olfactory cells. The current odor quality assessment standards emphasize human olfactory sensations, which is not only the lack of descriptive terms, but also difficult to achieve objective and impartial results due to physiological, psychological, environmental and other factors. Such component analysis methods as chromatography/mass spectrometry can detect hundreds or even thousands of chemical compositions, but the analysis process is quite complex, and the cost to do a measurement is very high. The more the components, the longer the analysis time. For example, the result of 4,000 to 5,000 chemical constituents in a cigarette smoke was obtained by chromatography/mass spectrometry analysis of American scholars and technicians for decades. Moreover, the relationship between the chemical compositions and the types and intensities of odors is seldom understood and grasped by people.

The core of an electronic nose instrument the gas sensor array has high sensitivity to the organic volatile gases such as hydrocarbons, alkenes, alcohols, esters, acids, aldehydes as well as the reducing inorganic gases such as CO and $NH_3$. In particular, it is worth noting that the $SnO_2$-type metal oxide semiconductor (MOS) gas sensors directly generate volt-level voltage response outputs to cigarette smokes without any secondary amplification, which is very attractive for the quality evaluation of tobacco and tobacco products. It is in this case that the electronic-nose-based instrumental methods for evaluating the qualities of tobacco and tobacco products are highly appreciated. It is expected that by using electronic nose instruments, tobacco and tobacco products can be identified, and their sensory quality indices such as aroma, harmony, impurity, irritation and aftertaste can be estimated in an objective and fair manner. On the basis, the process settings and technological parameters of tobacco in-process production can be optimized, and the quality grades of tobacco and tobacco products can be evaluated, and the method can be incorporated into the relevant industry and national standards for the quality evaluation of tobacco and tobacco products.

The characteristics of sensory quality evaluation of tobacco and tobacco products are that the first smoke gas is not the object of evaluation; there is a cigarette smoldering/self-sustaining combustion process between the first and the second smoke puff stages. In order to apply the electronic nose instruments and methods to the quality evaluation of tobacco and tobacco products, we need to solve the following problems.

(A), Selection of Gas Sensors and their Working Condition Optimization

The characteristics of cigarette smoke gases are as follows: (1) there are many and complex components; (2) some components have strong adhesion; (3) some trace-quantity components have a great impact on sensory perception. These are the basis for selection of gas sensors and optimization of their working conditions. On the one hand, the response speed of a gas sensor should be as fast as possible on the premise of necessary sensitivity; on the other hand, the contact time between gas sensors and one cigarette smoke gases should be as short as possible, the flushing flow rate of the ambient air should be as large as possible, and the flushing time should be as long as possible, so as to flush out the adhered smoke molecules as possible and avoid their attachment to the surface of sensitive films of gas sensors and the inner walls of pipelines, and the recovery of gas sensors should be as convenient and soon as possible.

(B), Precision Automation of Cigarette Smoke Sampling Process

Automation and simplicity of operation are particularly important for a tobacco electronic nose instrument. In order to simulate the evaluation process of assessors, we need to design a flameless igniter, invent a precise automatic cigarette smoke sampling system, design a smoke exhaust system, and make only the second smoke gas flow through the annular working chamber of the gas sensor array with the flow rate of 17.5 ml/s for 2 s. As a result, the smoke volume is 35 ml. In addition to the insertion of a tested cigarette sample into the cigarette holder and the removal and discarding of the residual butt, the whole process of smoke sampling is automatically completed by the tobacco electronic nose instrument.

(C), Modularization and Miniaturization of Key Components and Tobacco Electronic Nose Instrument We need to integrate the data acquisition card driving circuit, the gas sensor array working circuit, the DC power supply circuit and the driving circuits of multiple other components to form the drive and control circuit module. On the basis of integration of multiple two-position two-port electromagnetic valves and throttle valves, we need to invent and create a precise smoke sampling system module and miniaturize it. In order to facilitate installation and replacement, we also need to work on modularization and miniaturization of key components such as gas sensor array and multi-channel DC power supply.

(D), Integration of the Tobacco Electronic Nose Instrument

In order to make a tobacco electronic nose out of the laboratory, on the basis of modularization and miniaturization of key components, we need to solve the integration and miniaturization problem of the instrument. The ideal is to make the gas sensor array module, the precise smoke sampling module, the exhaust gas discharge module, the power supply module, the drive and control circuit module, the computer, the display unit as well as the peripherals be integrated in a small test box. A tobacco electronic nose instrument with small size, light weight and simple operation is designed and developed to facilitate on-site detection and the sensory quality index score estimation of tobacco and tobacco products.

(E), Machine Learning Method for On-Site Detection, Recognition and Sensory Quality Index Score Estimation of Large-Scale Tobacco and Tobacco Products There are many brands of cigarettes, many kinds of tobacco, and many kinds of tobacco flavors and fragrances. Recognition of cigarette brands is the basic functional requirement for a tobacco electronic nose instrument. On the basis of brand recognition, the electronic nose is further required to quantify and perform the score estimation of the sensory quality indices of tobacco and tobacco products, such as aroma, harmony, impurity, irritation, aftertaste, and so on, and to evaluate the quality grade accordingly. The above requirement will bring about the problem of large data processing and analysis, which challenges the existing machine learning methods. In order to apply the electronic nose instruments and methods for the sensory quality evaluation of tobacco and tobacco products, we need to invent new machine learning methods for the on-site detection, recognition and sensory quality index score estimation of large-scale tobacco and tobacco products.

The neural networks using the standard Sigmoid activation function $f(x)=1/(1+\exp(-x))$ usually transform the data sets to the range of [0, 1], which implies that the average of the actual components is about 0.5. If we transform the input components to a relatively large range, the interval between tobacco brands in the input space of samples can be enlarged appropriately, which is advantageous to accelerate the learning speed, and improve the learning accuracies and generalization abilities of neural networks.

For multi-class large-scale problems, the learning and generalization performance of the overall multi-input multi-output machine learning models are often unsatisfactory. For example, an integral multi-input multi-output neural network is easy to fall into local minima in the learning process. Moreover, the problem of simultaneous brand recognition and quantitative estimation of multiple sensory quality index scores for large-scale tobacco and tobacco products involves such two research directions in the field of machine learning: classification and nonlinear regression. Therefore, new machine learning models and algorithms need to be invented, including new task decomposition methods, new structure optimization methods, fast learning algorithms and decision-making methods.

SUMMARY

The disclosure is based on the relating disclosure patents: "Machine olfactory method for odor recognition based on modular combined neural networks" (China patent application No. 03141537.7), "Small-type automatic machine olfactory instrument and odor analysis method" (China patent application No. 200710036260.4). "Olfactory simulation instrument and qualitative/quantitative analysis method for multiple odors" (China patent application No. 2010115026.2), "Olfactory simulation instrument and on-site analysis method for determining odor grades of specific substances" (China patent application No. 201310315482.5). On the basis of the above-mentioned patent applications, an electronic nose instrument and an analysis method are provided to solve the problems of on-site automatic detection, recognition and sensory quality index scores estimation of tobacco and tobacco products.

In order to achieve the above purposes, the present disclosure is titled "Sensory quality evaluation method for tobacco and tobacco products using electronic nose instrument". The electronic nose instrument includes a gas sensor array module, an automatic smoke sampling system, a computer control and data analysis system, and an automatic ignition device, to realize the on-site detection, recognition and sensory quality index score estimation of tobacco and tobacco products.

The gas sensor array module includes 16 $SnO_2$ semiconductor gas sensors, which are evenly distributed in a sealed chamber having a middle diameter of $\phi$140 mm and a cross-section sized 20 mm×16 mm. The sealed chamber forms an annular working chamber of the gas sensor array. The annular working chamber is disposed in the thermostatic room with a constant temperature of 55±0.1° C. The gas sensor array module is arranged at a top right of the electronic nose instrument.

The automatic smoke sampling system includes a cigarette holder, a miniature vacuum pump, a first two-position two-port electromagnetic valve, a second two-position two-port electromagnetic valve, a third two-position two-port electromagnetic valve, a fourth two-position two-port electromagnetic valve, a fifth two-position two-port electromagnetic valve, a sixth two-position two-port electromagnetic valve, a first throttle valve and a second throttle valve, a flowmeter, gas pipelines and an overflow smoke gas discharge device. The automatic smoke sampling system is located at the lower right of the electronic nose instrument.

The automatic ignition device includes an ignition coil, a cigarette igniter head (also referred to as a cigarette-lighting head, a cigarette igniter or an ignition head), a movable iron core, an electromagnetic coil, a magnetic permeable iron frame, a compression spring, a spring seat, a cable, and a support. The automatic ignition device is set at a front right bottom of the electronic nose instrument.

The computer control and data analysis system includes a computer motherboard, a data acquisition card, a precision linear and switching power module, a drive and control circuit module, a hard disk, an internet card, a video card, and a monitor. The computer control and data analysis system being arranged on the left side of the electronic nose instrument. Optionally, the data acquisition card may be a 16-channel 16-bit high-precision data acquisition card.

The automatic smoke sampling system is configured to perform a smoke sampling period of 5 minutes for a tobacco and tobacco product sample. Depending on the type of gases, the gas sensor array is configured to undergo the following six stages: an early recovery stage of 210 s, a precise clean air calibration stage of 40 s, a balance stage of 2 s, a second smoke puff stage of 2 s, and an ambient air flushing stage of 46 s.

During a smoke sampling stage, under the computer control, the ignition coil in the automatic ignition device is configured to horizontally move 9 mm to the left and ignite the cigarette sample at 380° C. The miniature vacuum pump in automatic smoke sampling system is configured to suck the second smoke gas with a flow rate of 17.5 ml/sec, i.e., 1,050 ml/min, make the second smoke gas flow through the annular working chamber and sweep over surfaces of sensitive films of the gas sensors for a duration of 2 s, so that the gas sensor array produces a sensitive response. From the beginning of the balance stage, the computer control and data analysis system is configured to begin to sequentially record the voltage response data of the gas sensor array generated in the three stages: the balance stage of 2 s, the second smoke puff stage of 2 s and the ambient air flushing stage of 36 s, with a total data recording duration of 40 s. In the remaining time of the 5-minute smoke sampling period, the voltage response data is not recorded.

Within the data recording duration of 40 s, the steady-state maximum voltage value in the response curve of a single gas sensor to the second smoke gas is extracted as a feature component, and thus the array of 16 gas sensors generates a 16-dimensional voltage response vector. Within 10 s after the end of the data recording, the computer control and data analysis system is configured to perform the recognition of brand, origin of manufacture, and authenticity of tobacco and tobacco products, and further perform, based on the 16-dimensional voltage response vector, the score estimation of the five sensory quality indices: aroma, harmony, impurity, irritation and aftertaste.

The computer control and data analysis system is further configured to employ the cascade modular neural network model to identify tobacco and tobacco product samples, and estimate their sensory quality index scores. The first level of the cascade modular neural network model is comprised of n(n−1)/2 single-output neural networks arranged in parallel, forming n vote recognition groups which are configured to identify n kinds of tobacco and tobacco products, including brand, origin of manufacture, and authenticity. The second level of the cascade modular neural network model is comprised of n×5 single-output neural networks, and each score estimation group is comprised of 5 single-output neural networks, to perform the score estimation of the five sensory quality indices: aroma, harmony, impurity, irritation and aftertaste, for the n kinds of tobacco and tobacco products.

An angle between the axis of the cigarette holder and the horizontal plane is 0 to 5 degrees. Before the automatic ignition, an operator inserts the butt of a cigarette sample into the cigarette holder at a depth of 9±0.5 mm, and the inserting operation lasts 15 s. Within 15 s after the end of the second smoke puff stage, the operator removes the remaining cigarette butt from the cigarette holder, extinguishes and discards it.

The ignition coil of the automatic ignition device is operated with a 24V working voltage and a 5A current. The axes of the cigarette igniter head, the movable iron core, the electromagnetic coil, the compression spring and the cigarette holder are at a same horizontal line. Under the computer control, starting from the fifth second before the first smoke puff stage, the ignition coil is energized and heated to 380° C. within 5 s. Meanwhile, the electricity of the electromagnetic coil is cut off, and under the action of compression spring, the ignition coil on the cigarette-lighting head is configured to move 9 mm horizontally from a reference position to the left and ignite the cigarette sample. After sucking the first smoke gas for 1 s, the ignition coil is switched off, and the electromagnetic coil is energized. Under the action of electromagnetic force of the electromagnetic coil, the ignition coil is disengaged from the ignited cigarette sample and returns to the reference position.

Under the suction action of the miniature vacuum pump, the first smoke gas is directly discharged to outdoor after sequentially passing through the second two-position two-port electromagnetic valve, the first throttle valve and the flowmeter with a flow rate of 17.5 ml/s, i.e., 1,050 ml/min completely without passing through the annular working chamber. The process lasts 2 s and a 35 ml volume of smoke gas is sucked. Next, the ignited cigarette sample is smoldered/self-sustaining combustion for 20 s.

Under the suction of the miniature vacuum pump, the second smoke gas is forced to flow in sequence through the first two-position two-port electromagnetic valve, the annular working chamber, the fifth two-position two-port electromagnetic valve, the first throttle valve, and the flowmeter with a flow rate of 17.5 ml/s, i.e., 1,050 ml/min, and is discharged outdoor. The process lasts 2 s and a 35 ml volume of smoke gas is collected.

The precise clean air calibration stage is simultaneously carried out with the stage of a cigarette insertion stage, an automatic ignition stage, a first smoke puff stage, and a smoldering/self-sustaining combustion stage, both stages last 40 s at the same time. In the precise clean air calibration stage, the clean air flows in sequence through the second throttle valve, the sixth two-position two-port electromagnetic valve, the annular working chamber, the third two-position two-port electromagnetic valve and is finally discharged to outdoor, with a flow rate of 17.5 ml/s. The following operations are performed in order: (1) the tested cigarette sample is inserted into the cigarette holder by the operator within 15 s; (2) the ignition coil of the automatic ignition device is energized, shifted 9 mm left to contact the cigarette sample, and is heated up to 380° C. within 5 s; (3) the first smoke puff stage lasting 2 s; and (4), the cigarette sample smoldering/self-sustaining combustion lasting 18 s.

As soon as the second smoke puff stage with a flow rate of 1,050 ml/min is completed, the ambient air flushing stage with a flow rate of 6,500 ml/min begins. The ambient air sequentially flows through the third two-position two-port electromagnetic valve, the annular working chamber of the gas sensor array, the fifth two-position two-port electromagnetic valve, the fourth two-position two-port electromagnetic valve, and is finally discharged to outdoor, which lasts 15 s. During this time slot, the residual cigarette butt is removed and discarded by the operator. After that, the ambient air sequentially flows through the first two-position two-port electromagnetic valve, the annular working chamber, the fifth two-position two-port electromagnetic valve and the fourth two-position two-port electromagnetic valve with a flow rate of 6,500 ml/min, and is eventually discharged to outdoor, which lasts 31 s. At the end of the 31 s process, the detection period of a cigarette sample ends. If next sample needs to be detected, the computer system is configured to automatically start a new detection period and automatically transfer to the early recovery stage; otherwise, the operator clicks an "End detection" button in the screen drop-down menu to end the detection process.

In the data acquisition stage, the tobacco electronic nose instrument is configured to test the standard samples of tobacco and tobacco products which have been evaluated by the assessor panel and given the sensory quality index scores. The measurement period of a single standard sample is 5 minutes. The steady-state maximum voltage value of the response curve of each gas sensor to the second smoke gas is extracted as the feature component, and thus a 16-dimensional voltage response vector $x_p'$ is obtained to be $x_p' = (x_{p1}', \ldots, x_{pi}', \ldots, x_{p16}')^T \in R^{16}$ for the $p^{th}$ standard sample, where the 16-dimensional voltage response vector $x_p'$ is also referred to as a voltage response vector $x_p'$ or a voltage response pattern $x_p'$. According to testing N standard samples by using the gas sensor array of the electronic nose instrument, the standard voltage response dataset $X' \in R^{N \times 16}$ is obtained, and the corresponding relationship is established between each 16-dimensional voltage response vector $x_p'$ and scores of five sensory quality indices including aroma $d_1 \in R^N$, harmony $d_2 \in R^N$, impurity $d_3 \in R^N$, irritation $d_4 \in R^N$ and aftertaste odor $d_5 \in R^N$. 10 standard samples are measured for each brand with 3 grades: A, B and C. If the brand number is n, then N=30n.

All feature variables of the standard voltage response dataset X' of the gas sensor array to the standard samples are transformed to the range of [0.0, 6.0] by the positive proportional preprocess. Let the steady-state maximum voltage value of the response curve of the gas sensor i to the $p^{th}$ standard sample be $x_{pi}'$, and the value after proportional transformation is:

$$x_{pi} = 6 \times \frac{x_{pi}' - \min(X')}{\max(X') - \min(X')} \quad (1)$$

where max(X') and min(X') are the maximum and minimum values of the standard voltage response dataset X', respectively, $x_{pi}$ is a transformed steady-state maximum voltage value of the response curve of the gas sensor i to the $p^{th}$ standard sample after a proportional transformation. The voltage response vector $x_p'$ is thus changed to a 16-dimensional pattern $x_p = (x_{p1}, \ldots, x_{pi}, \ldots, x_{p16})^T \in R^{16}$, where 16-dimensional pattern $x_p$ is also referred to as a training pattern $x_p$ or a pattern $x_p$ in the present disclosure. The values of max(X') and min(X') are saved in the computer as the basic parameter. After the standard voltage response dataset X' is proportionally transformed, the new dataset is called a training set and denoted as X.

In the recognition and sensory quality index score estimation stage for the undetermined cigarette pattern x, the max(X') and min(X') are still used to proportionally transform the steady-state maximum voltage value of the response curve $x_{pi}'$ of the response curve of the gas sensor i by using formula (1).

Each single-output neural network in the cascade modular neural network model goes through the learning stage for the training set X, and the recognition and sensory quality index score estimation stage for the undetermined cigarette pattern x.

In the learning stage of the first level of the cascade modular neural network model, i.e., n(n−1)/2 single-output neural networks, the training set X is firstly implemented an one-against-one (OAO) decomposition and is decomposed into $C_n^2 = n(n-1)/2$ binary-class training subsets, and then, the n(n−1)/2 binary-class training subsets are learned by n(n−1)/2 single-output neural networks one by one, using the error back-propagation algorithm. The single-output neural networks are single-hidden-layer in structure, the number of input nodes is m=16, the number of hidden nodes is $s_1$=8, and the number of output nodes is 1. The target output is encoded in {0.0, 3.0}, and the activation functions of all hidden nodes and output nodes are $f(\varphi) = 3(1+\exp(-\varphi))^{-1}$.

where the binary-class training subset of the two brands $\omega_j$ and $\omega_k$ is $X_{jk} = \{X_j, X_k\}$, obtained by measuring all the standard samples of the two brands $\omega_j$ and $\omega_k$ by the electronic nose instrument, and learned by the single-output neural network $\overline{\omega}_{jk}$. The number of samples thus is $N_{jk} = N_j + N_k = 60$, and the learning factor is $\eta_{jk} = 10/N_{jk} = 0.17$.

For the training pattern $x_p = (x_{p1}, \ldots, x_{pi}, \ldots, x_{p16})^T \in R^{16}$, the actual output of the hidden node h in the single-output neural network $\overline{\omega}_{jk}$ is:

$$\xi_{ph}^{(jk)} = f(\varphi_{ph}^{(jk)} = 3(1+\exp(-\varphi_{ph}^{(jk)}/3)) \quad (2)$$

where $\varphi_{ph}^{(jk)}$ is the weighted sum of all input components of the pattern $x_p$ for the hidden node h:

$$\varphi_{ph}^{(jk)} = \theta_h^{(jk)} + w_{h1}^{(jk)} x_{p1} + \ldots + w_{hi}^{(jk)} x_{pi} + \ldots + w_{h,16}^{(jk)} x_{p,16} = \sum_{i=0}^{16} w_{hi}^{(jk)} x_{pi} \quad (3)$$

Here, the threshold term is $\theta_h^{(jk)} = w_{h0}^{(jk)}$, and the constant term is $x_{p0} = 6.0$.

The actual output of the single-output neural network $\overline{\omega}_{jk}$ for the training pattern $x_p$ is:

$$y_p^{(jk)} = f(\phi_p^{(jk)}) = 3(1+\exp(-\phi_p^{(jk)}/3))^{-1} \quad (4)$$

In formula (4), $\phi_p^{(jk)}$ is the weighted sum of outputs of all hidden nodes of the single-output neural network $\overline{\omega}_{jk}$, that is:

$$\phi_p^{(jk)} = \theta^{(jk)} + w_1^{(jk)} \xi_{p1}^{(jk)} + \ldots + w_1^{(jk)} \xi_{ph}^{(jk)} + \ldots + w_8^{(jk)} \xi_{p8}^{(jk)} = \sum_{h=0}^{8} w_h^{(jk)} \xi_{ph}^{(jk)} \quad (5)$$

where the threshold term is $\theta^{(jk)} = w_0^{(jk)}$, and the constant term is $\xi_{p0}^{(jk)} = +3.0$.

In the learning stage of the second level of the cascade modular neural network model, i.e., n×5 single-output neural networks, the training set X is decomposed into n binary-class training subsets. Each binary-class training subset is comprised of all patterns from a single tobacco brand, namely $N_j = 30$. Each of score estimation groups is comprised of five single-output neural networks, which respectively fit the non-linear relations between the responses of gas sensor array and the scores of five sensory quality indices, namely, aroma, harmony, impurity, irritation and aftertaste, for the corresponding brand. Each single-output neural network is a single-hidden-layer in structure, the number of input nodes is m=16, the number of hidden nodes is $s_1$=8 and the number of output nodes is 1. The activation function of all hidden and output nodes is still the same as the previous, i.e., $f(\varphi) = 3(1+\exp(-\varphi/3))^{-1}$. The learning rate is $\eta_j = 5/N_j = 0.17$, and the back-propagation learning algorithm is still used.

Let the training subset $X_j$ be composed of $N_j = 30$ samples from only the brand $\omega_j$; five single-output neural networks in the score estimation group $\Lambda_j$ fit the non-linear relations between the training subset $X_j$ and scores of the five sensory quality indices of the brand $\omega_j$, namely, aroma, harmony, impurity, irritation, and aftertaste. The target outputs of the training subset $X_j$ are the sensory quality index scores of the brand $\omega_j$, which is proportionally transformed to the range of [0.15, 2.85].

For the pattern $x_p$ from the brand $\omega_j$, supposed that the $r^{th}$ sensory quality index score is $d_p^{(jr)'}$, the target output of the $r^{th}$ single-output neural network after proportional transformation is:

$$d_p^{(jr)} = 0.15 + 2.70 \times \frac{d_p^{(jr)'} - \min(d^{(jr)'})}{\max(d^{(jr)'}) - \min(d^{(jr)'})} \qquad (6)$$

where $d^{(jr)'} = (d_1^{(jr)'}, \ldots, d_p^{(jr)'}, \ldots, d_{30}^{(jr)'})^T$ is the $r^{th}$ sensory quality index score vector for all $N_j = 30$ standard samples of the brand $\omega_j$.

The actual output of the hidden node h of the $r^{th}$ single-output neural network in the score estimation group $\Lambda_j$ is:

$$\xi_{ph}^{(jr)} = f(\varphi_{ph}^{(jr)}) = 3(1 + \exp(-\varphi_{ph}^{(jr)}/3))^{-1} \qquad (7)$$

In formula (7), $\varphi_{ph}^{(jr)}$ is the weighted sum of all input components of the training pattern $x_p$ for the hidden node h, or:

$$\varphi_{ph}^{(jr)} = \theta_h^{(ph)} + w_{h1}^{(jr)} x_{p1} + \ldots + w_{hi}^{(jr)} x_{pi} + \ldots + w_{h,16}^{(jr)} x_{p,16} = \sum_{i=0}^{16} w_{hi}^{(jr)} x_{pi} \qquad (8)$$

where the threshold term is $\theta_h^{(jr)} = w_{h0}^{(jr)}$, and the constant term is $x_{p0} = 6.0$.

The actual output of the $r^{th}$ single-output neural network in the score estimation group is:

$$z_p^{(jr)} = f(\phi_p^{(jr)}) = 3(1 + \exp(-\phi_p^{(jr)}/3))^{-1} \qquad (9)$$

In formula (9), $\phi_p^{(jr)}$ is the weighted sum of real outputs of all hidden nodes of the $r^{th}$ single-output neural network:

$$\phi_p^{(jr)} = \theta^{(jr)} + w_1^{(jr)} \zeta_{p1}^{(jr)} + \ldots + w_1^{(jr)} \zeta_{ph}^{(jr)} + \ldots + w_8^{(jr)} \zeta_{p8}^{(jr)} = \sum_{h=0}^{8} w_h^{(jr)} \zeta_{ph}^{(jr)} \qquad (10)$$

where the threshold term is $\theta^{(jr)} = w_0^{(jr)}$, and the constant term is $\xi_{p0}^{(jr)} = +3.0$.

The first level of the cascade modular neural network model for recognizing tobacco and tobacco products is that each vote recognition group consists of (n−1) single-output neural networks, representing a specified brand of tobacco and tobacco product, and the maximum number of votes is (n−1). Each single-output neural network must and just join in two of the n vote recognition groups, and n(n−1)/2 single-output neural networks therefore constitute n vote recognition groups, respectively. The majority vote rule is used for decision-making.

The single-output neural network $\overline{\omega}_{jk}$ must join in the vote for the $j^{th}$ vote recognition group $\Omega_j$ and the $k^{th}$ vote recognition group $\Omega_k$. In the $j^{th}$ vote recognition group $\Omega_j$, if the actual output of $\overline{\omega}_{jk}$ satisfies $y^{(jk)} > 1.5$, the probability of estimating an undetermined cigarette pattern x to belong to the brand $\omega_j$ obtains 1 vote; in the $k^{th}$ vote recognition group $\Omega_k$, if $y^{(jk)} < 1.5$, the probability of belonging to the brand $\omega_k$ obtains 1 vote.

The decision rule is that the undetermined cigarette pattern x belongs to the brand represented by the vote recognition group with the highest number of votes in the n vote recognition groups. If two or more vote recognition groups have the equal and highest vote number, the decision-making is that the undetermined cigarette pattern x does not belong to any existing brand.

The second level of the cascade modular neural network model for performing the sensory quality index score estimation of tobacco and tobacco products is that each score estimation group consists of five single-output neural networks, which is responsible for performing the score estimation of the five sensory quality indices of a corresponding brand, namely, aroma, harmony, impurity, irritation and aftertaste. n×5 single-output neural networks are divided into n score estimation groups, which corresponds to n vote recognition groups with the one-by-one relationship.

In the stage of the five sensory quality index scores of the undetermined cigarette pattern x, on the premise that the vote recognition group $\Omega_j$ in the first level of the cascade modular neural network model gets the largest number of votes, the score estimation group $\Lambda_j$ in the second level, representing the brand $\omega_j$, takes part in the estimation alone, while the other score estimation groups do not need to.

Suppose the actual output $\Lambda_j$ of the $r^{th}$ single-output neural network in the score estimation group is $z^{(jr)}$, the estimated score of the $r^{th}$ sensory quality index of the brand $\omega_j$ is:

$$z^{(jr)'} = (z^{(jr)} - 0.15) \times \frac{\max(d^{(jr)'}) - \min(d^{(jr)'})}{2.70} + \min(d^{(jr)'}) \qquad (11)$$

If a new brand is added to the n existing brands, only n single-output neural networks need to be added to the first level of cascade modular neural network model and learnt, and the number of the single-output neural networks of the first level is thus increased from the existing n(n−1)/2 to n(n+1)/2. For example, for the added brand $\omega_{n+1}$, the newly added and learnt single-output neural networks are $\omega_{1(n+1)}, \ldots, \overline{\omega}_{j(n+1)}, \ldots, \overline{\omega}_{n(n+1)}$.

Correspondingly, to perform the sensory quality index score estimation for a newly added brand, five new single-output neural networks are added to the second level of the cascade modular neural network model and learnt, i.e., the number of the single-output neural networks of the second level is increased from the existing n×5 to (n+1)×5. A fake brand or an existing same brand produced by another manufacturer is regarded as a separate brand for recognition and sensory quality index score estimation.

The detection, recognition and sensory quality index score estimation operations of the electronic nose instrument for cigarette samples includes the following stages:

(1), A power-on stage: The instrument is preheated for 30 minutes, and the ambient air sequentially flows through the first two-position two-port electromagnetic valve, the annular working chamber of the gas sensor array, the fifth two-position two-port electromagnetic valve, and the fourth two-position two-port electromagnetic valve with a flow rate of 6,500 ml/min, and is eventually discharged to outdoor. A thermostatic room is raised from a room temperature to a constant temperature of 55±0.1° C.

(2), A smoke sampling stage: The operator clicks the "Start detection" button in the screen drop-down menu, and the instrument enters the smoke sampling period lasting 5 minutes. The computer automatically generates a text file named "xxx" in the designated folder to record the response data of the gas sensor array to the smoke.

(3), An early recovery stage: Within the 0.00-210.00 s time interval of the smoke sampling period, the ambient air sequentially flows through the first two-position two-port electromagnetic valve, the annular working chamber, the fifth two-position two-port electromagnetic valve and the fourth two-position two-port electromagnetic valve with the flow rate of 6,500 ml/min, and is finally discharged to outdoor. Under the flushing role of the 6,500 ml/min ambient air, the smoke molecules adhered onto the surfaces of sensitive films of gas sensors and the inner walls of pipelines are flushed away tentatively, and the gas sensor array is restored to the reference state preliminarily, lasting 210 s.

(4), A precise clean air calibration stage: Within the 210.00-250.00 s time interval of the smoke sampling period, the two following stages are carried out simultaneously: (a) the precise clean air calibration stage, and (b) a cigarette insertion stage, an automatic ignition stage, a first smoke puff stage, and a smoldering/self-sustaining combustion stage. The two stages last 40 s at the same time.

(4a), The precise clean air calibration stage: a clean air sequentially flows through the second throttle valve, the sixth two-position two-port electromagnetic valve, the annular working chamber, and the third two-position two-port electromagnetic valve with a flow rate of 17.5 ml/s, i.e., 1,050 ml/min, and is finally discharged to outdoor for 40 s. Clean air makes the gas sensor array return to the reference state accurately.

(4b.1), The cigarette insertion stage: within the 210.00-225.00 s time interval of the smoke sampling stage, i.e., the first 15 s time slot of the precise clean air calibration stage, the screen displays the word "Cigarette insertion", and the operator inserts the filter end of the tested cigarette sample into the cigarette holder, at the insertion depth of 9.0±0.5 mm.

(4b.2), The automatic ignition stage: in the 225.00-231.00 s time interval of the smoke sampling period, i.e., the 15.00-21.00 s time slot of the precise clean air calibration stage, the ignition coil is energized. At the same time, the ignition head moves 9 mm to the left so that the ignition coil contacts and ignites the tested cigarette sample for 6 s. In the 231.00-269.00 s time interval of the smoke sampling period, the electromagnetic coil is powered, and the ignition coil is powered off and returned to the reference position, lasting 38 s, including the later is of the first smoke puff stage, 18 s of the smoldering/self-sustaining combustion stage, 2 s of the balance stage, 2 s of the second smoke puff stage, and 15 s of the residual butt removal stage.

(4b.3), The first smoke puff stage: in the 230.00-232.00 s time interval of the smoke sampling period, i.e., the 20.00-22.00 s time slot of the precise clean air calibration stage, under the suction of the miniature vacuum pump, the smoke gas sequentially flows through the second two-position two-port electromagnetic valve, the first throttle valve and the flowmeter with a flow rate of 17.5 ml/s, i.e., 1,050 ml/min, and is directly discharged to outdoor, which lasts 2 s.

(4b.4), The smoldering/self-sustaining combustion stage: in the 232.00-250.00 s time interval of the smoke sampling period, i.e., the 22.00-40.00 s time slot of the precise clean air calibration stage, the second two-position two-port electromagnetic valve is disconnected, and the tested cigarette sample enters the smoldering/self-sustaining combustion stage, lasting 18 s.

(5), A balance stage: within the 250.00-252.00 s time interval of the smoke sampling period, all two-position two-port electromagnetic valves are disconnected. No gas flows in the annular working chamber of the gas sensor array. The tested cigarette sample is still in the smoldering/self-sustaining combustion stage, lasting 2 s.

(6), A second smoke puff stage: within the 252.00-254.00 s time interval of the smoke sampling period, the first two-position two-port electromagnetic valve and the fifth two-position two-port electromagnetic valve are connected, and the other four two-position two-port electromagnetic valves are disconnected. The flow rate of cigarette smoke is 17.5 ml/s, i.e., 1,050 ml/min, through the first two-position two-port electromagnetic valve, the annular working chamber of the gas sensor array, the fifth two-position two-port electromagnetic valve, the first throttle valve and the flowmeter sequentially, and is finally discharged to outdoor, which lasts 2 s and thus a 35 ml volume of smoke gas is collected.

(7), An ambient air flushing stage: in the 254.00-300.00 s time interval of the smoke sampling period, the indoor ambient air flows through the annular working chamber of the gas sensor array with a flow rate of 6,500 ml/min. The smoke molecules adhered to the surfaces of the sensitive films of gas sensors and the inner walls of pipelines are roughly flushed away, and the gas sensor array enters the early recovery stage, which includes the following two stages: a residual cigarette butt removal stage and a post removal stage:

(7.1), The residual cigarette butt removal stage: within the 254.00-269.00 s time interval of the smoke sampling period, the operator takes out the residual cigarette butt and discards it within 15 s. During this 15 s duration, the third, the fourth and the fifth two-position two-port electromagnetic valves are turned on, the remaining three two-position two-port electromagnetic valves are switched off, and the ambient air flows through the third two-position two-port electromagnetic valve, the annular working chamber of the gas sensor array, the fifth two-position two-port electromagnetic valve and the fourth two-position two-port electromagnetic valve with the flow rate of 6,500 ml/min, and is finally discharged to outdoor, lasting 15 s.

(7.2) The post removal stage: within the 269.00-300.00 s time interval of the smoke sampling period, the first, the fourth and the fifth two-position two-port electromagnetic valves are connected, and the remaining three two-position two-port electromagnetic valves are disconnected. The ambient air flows through the first two-position two-port electromagnetic valve, the annular working chamber of the gas sensor array, the fifth two-position two-port electromagnetic valve and the fourth two-position two-port electromagnetic valve, and is finally discharged to outdoor, lasting 31 s. At this stage, the positions of the first to sixth two-position two-port electromagnetic valves and the flow rate of ambient air are exactly the same as the early recovery stage of the gas sensor array.

(8), A data recording stage: from the time point of 250.00 s in the smoke sampling period, i.e., from the beginning of the balance stage, the computer saves the voltage responses of 16 gas sensors in a "xxx" text file through the 16-channel 16-bit high-precision data acquisition card until the time point of 290.00 s, i.e., the time point of 36.00 s of the ambient air flushing stage, including the second smoke puff stage, the residual cigarette butt removal stage and the post removal stage. The duration of data recording is 40 s after the residual cigarette butt removal stage.

(9), A feature extraction stage: in a smoke sampling period, the computer control and data analysis system extracts the steady-state maximum voltage value in the response curve of each gas sensor from the "xxx" data recording file, which is 40 s long, as the response component, essentially the response to the second smoke puff, and thus a tobacco and tobacco product sample is transformed into a 16-dimensional measurement pattern, and saved in the data set file of tobacco and tobacco product samples in the hard disk.

(10), A recognition and sensory quality index score estimation stage: within the 290.00-300.00 s time interval of the smoke sampling period, or 10 s after the end of the data recording stage, the first level of the cascade modular neural network model, i.e., the n vote recognition groups, determines the brand, origin and authenticity of a tested sample according to the majority vote rule; and the score estimation group in the second level of the cascade modular neural network model corresponding to the winning vote recognition group performs the score estimation of the five sensory quality indices, namely, aroma, harmony, impurity, irritation and aftertaste, and the recognition and score estimation results are displayed on the monitor.

By repeating the steps (2)-(10), the tobacco electronic nose instrument realizes smoke detection, recognition and sensory quality index score estimation for a plurality of tobacco and tobacco product samples. A complete test period for a tobacco and tobacco product sample takes 300 s.

BRIEF DESCRIPTION OF THE DRAWINGS

FIG. 11 illustrates an on-off and duration diagram of six two-position two-port electromagnetic valves, ignition coil and electromagnetic coil in a smoke sampling period of 300 s according to the present disclosure named a sensory quality evaluation method for tobacco and tobacco products using an electronic nose instrument.

FIG. 15a illustrates a first-order partial derivative curves (solid line) of the first-order partial derivative $\partial f(\varphi)/\partial \varphi$ of the modified Sigmoid activation function $f(\varphi)=3/(1+\exp(-\varphi/3))$ and a first-order partial derivative curves (dashed line) of the first-order partial derivative $\partial f_0(\varphi)/\partial \varphi$ of the standard Sigmoid activation function $f_0(\varphi)=1/(1+\exp(-\varphi))$ in the interval $[-10,10]$ according to the present disclosure named a sensory quality evaluation method for tobacco and tobacco products using an electronic nose instrument.

FIG. 15b illustrates a ratio change curve of the first-order partial derivative $\partial f(\varphi)/\partial \varphi$ of the modified Sigmoid activation function $f(\varphi)=3/(1+\exp(-\varphi/3))$ and the first-order partial derivative $\partial f_0(\varphi)/\partial \varphi$ of the standard Sigmoid activation function $f_0(\varphi)=1/(1+\exp(-\varphi))$ in the interval $[-10,10]$ according to the present disclosure named a sensory quality evaluation method for tobacco and tobacco products using an electronic nose instrument.

FIG. 16 illustrates a situation of $n(n-1)/2$ single-output neural networks to be divided into n vote recognition groups when determining the brand ownership of a tested cigarette sample according to the present disclosure named a sensory quality evaluation method for tobacco and tobacco products using an electronic nose instrument.

DETAILED DESCRIPTION

The detailed description of the present disclosure is further given below in conjunction with the accompanying drawings.

Figure 1:
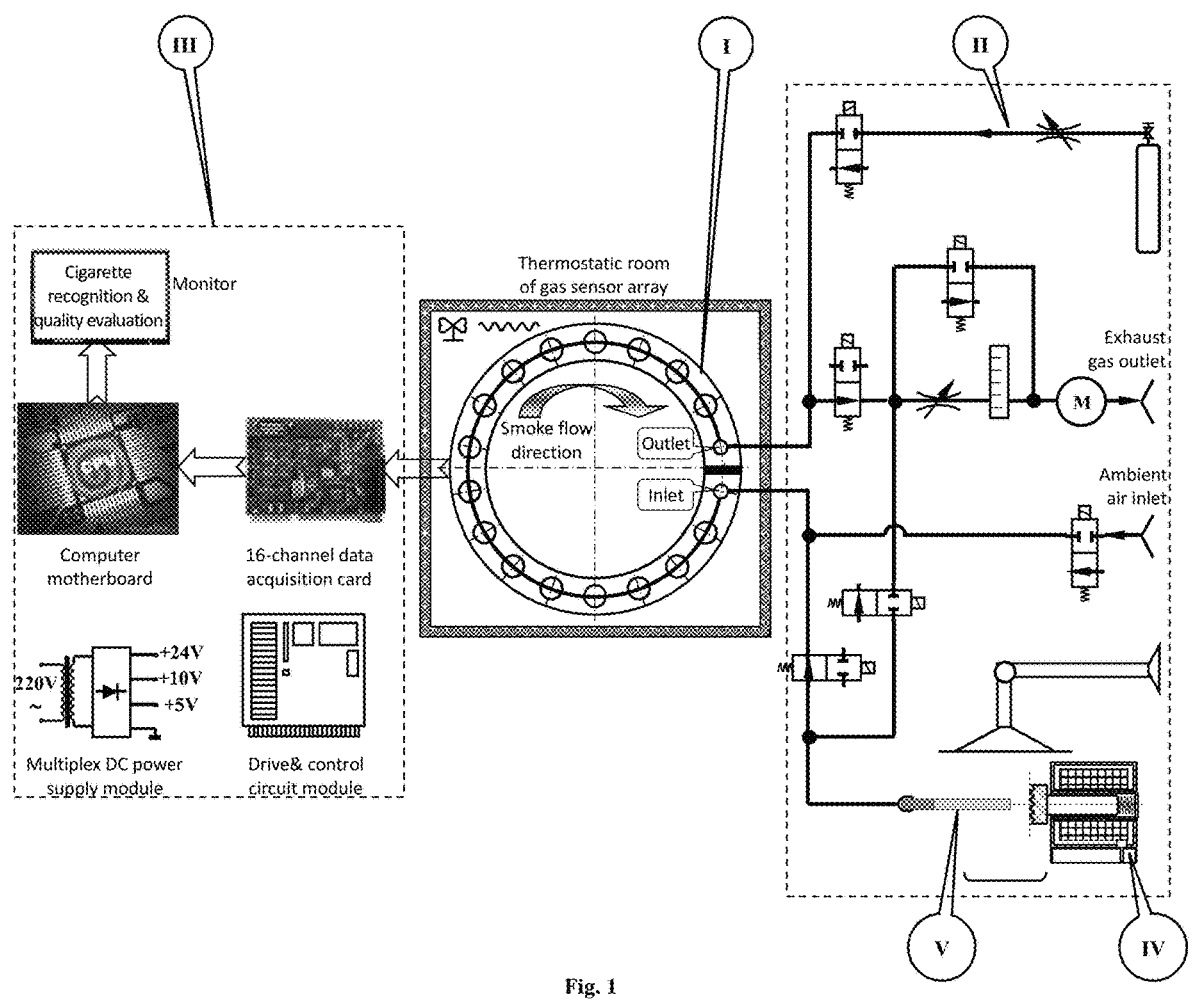
FIG. 1 illustrates a working principle diagram of the tobacco electronic nose instrument (under a second smoke puff stage) according to the present disclosure named a sensory quality evaluation method for tobacco and tobacco products using an electronic nose instrument.
Figure 2:
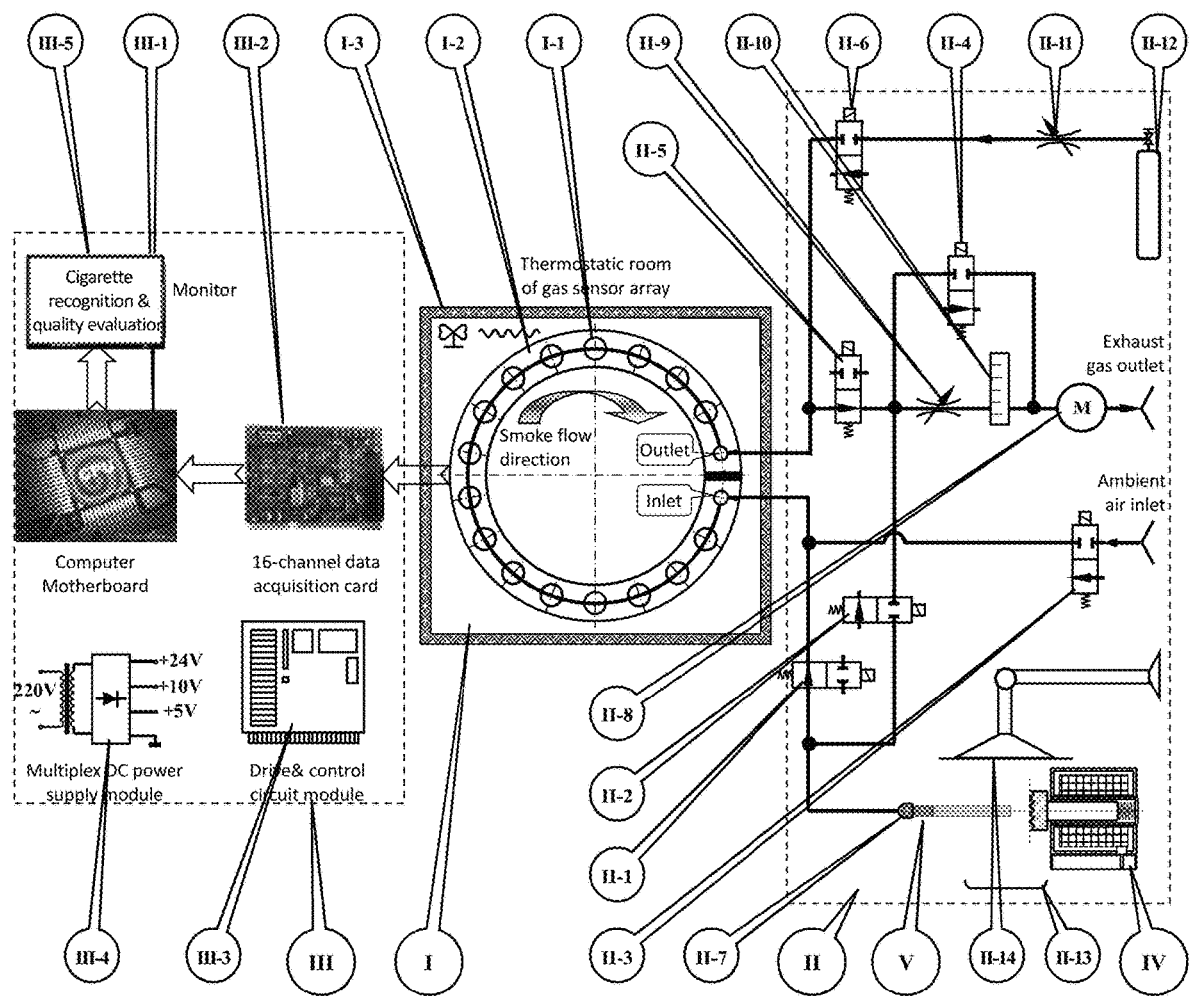
FIG. 2 illustrates a working principle diagram of the tobacco electronic nose instrument (under a second smoke puff stage), that is a numbering diagram of major parts and components, according to the present disclosure named a sensory quality evaluation method for tobacco and tobacco products using an electronic nose instrument.

FIG. 1 illustrates the working principle diagram of the tobacco electronic nose instrument. The gas paths and the two-position two-port electromagnetic valves at this moment are in the working state of the second smoke puff. The tobacco electronic nose instrument includes the gas sensor array module (I), the automatic smoke sampling system (II), the computer control and data analysis system (III), the automatic ignition device (IV) and the tested cigarette sample (V). FIG. 2 illustrates the numbering of the main components of the tobacco electronic nose instrument.

The main components of the gas sensor array module (I) include: the gas sensor array (I-1), the annular working chamber (I-2), the thermal insulation layer (I-3), as well as the resistance heating wire and the fan, located in the upper right part of the tobacco electronic nose instrument. Among them, the gas sensor array (I-1) mainly consists of 16 gas sensors of TGS800 and TGS2000 series, and the available models include TGS800, TGS813, TGS816, TGS821, TGS822, TGS823, TGS826, TGS830, TGS832, TGS2600, TGS2602, TGS2603, TGS2610, TGS2611, TGS2612, TGS2620, TGS3830, TGS2201, and PID-A1 photoionic detector. The function of the gas sensor array module (I) is to convert a cigarette smoke gas with complex components into the analog voltage signals of [0-10V].

The main components of the automatic smoke sampling system (II) include: the first two-position two-port electromagnetic valve (II-1), the second two-position two-port electromagnetic valve (II-2), the third two-position two-port electromagnetic valve (II-3), the fourth two-position two-port electromagnetic valve (II-4), the fifth two-position two-port electromagnetic valve (II-5), the sixth two-position two-port electromagnetic valve (II-6), the cigarette holder (II-7), the miniature vacuum pump (II-8), the first throttle valve (II-9), the flowmeter (II-10), the second throttle valve (II-11), the clean air (II-12), the ash tray (II-13), and the overflow smoke gas discharge device (II-14). The automatic smoke sampling system (II) is located at the bottom right part of the electronic nose instrument.

The main components of the computer control and data analysis system (III) are: the computer motherboard (III-1), the 16-channel data acquisition card (III-2), the drive and control circuit module (III-3), the multi-channel DC voltage module (III-4) (also referred to as precision multi-channel linear and switching power module), the monitor (III-5), the hard disk, the network card, the graphics card, the mouse, the keyboard and so on. The computer control and data analysis system (III) is located on the left of tobacco electronic nose instrument. The main functions of the computer control and data analysis system (III) are: (1) acquisition, analysis and processing of gas sensor array response signals; (2) drive and control of multiple two-position two-port electromagnetic valves and the miniature vacuum pump, the automatic ignition device (IV), and including the computer control and data analysis system (III) itself.

Figure 3:
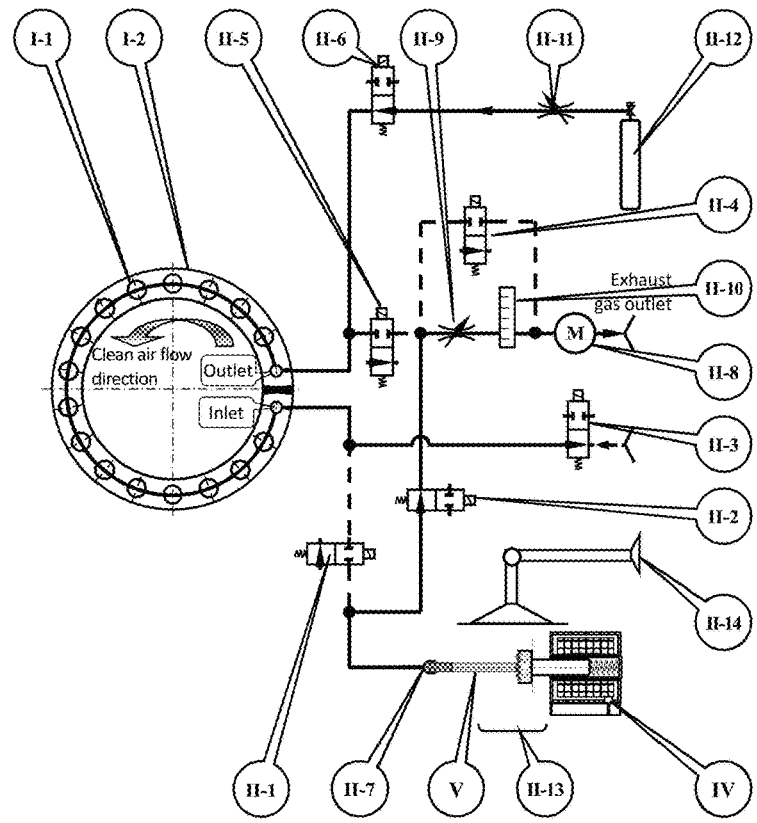
FIG. 3 illustrates a schematic diagram of on-off state of multiple two-position two-port electromagnetic valves and gas paths (a precise clean air calibration stage, an automatic ignition sage of cigarette sample and a first smoke puff stage) according to the present disclosure named a sensory quality evaluation method for tobacco and tobacco products using an electronic nose instrument.

FIG. 3 is a schematic diagram illustrating the on-off state of the two-position two-port electromagnetic valves and the gas paths when the precise clean air calibration stage, the automatic ignition stage of a cigarette sample and the first smoke puff stage are being carried out. Under this condition, the tobacco electronic nose instrument should complete the following stages: the ignition stage of the tested cigarette sample (V), the first smoke puff stage by the automatic smoke sampling system (II), and the precise clean air calibration stage of the gas sensor array (I-1).

In the automatic ignition stage of the tested cigarette sample (V) and the first smoke puff stage of the automatic smoke sampling system (II), the second two-position two-port electromagnetic valve (II-2) is turned on, the first two-position two-port electromagnetic valve (II-1), the fourth two-position two-port electromagnetic valve (II-4) and the fifth two-position two-port electromagnetic valve (II-5) are disconnected. In the automatic ignition stage, the ignition coil (IV-1) of the automatic ignition device (IV) is energized, the electromagnetic coil (IV-4) is cut off, and the valve core (IV-3) moves 9 mm horizontally to the left under the role of the compression spring (IV-6), which makes the ignition coil (IV-1) contact with the tested cigarette sample (V) for 5 s. Subsequently, in the first smoke puff stage, the smoke gas does not pass through the gas sensor array module (I) at all, but is directly discharged to outdoor for 2 s, with the flow rate of 17.5 ml/s, i.e. 1,050 ml/min, equivalent to 35 ml smoking gas, under the suction role of miniature vacuum pump (II-8), through the second two-position two-port electromagnetic valve (II-2), the first throttle valve (II-9) and the flowmeter (II-10).

While the tested cigarette sample (V) is automatically ignited and the first smoke gas is sucked by the automatic smoke sampling system (II), the gas sensor array (I-1) is in the precise clean air calibration stage. The third two-position two-port electromagnetic valve (II-3) and the sixth two-position two-port electromagnetic valve (II-6) are connected, and the clean air sequentially flows through the second throttle valve (II-11) and the sixth two-position two-port electromagnetic valve (II-6), the annular working chamber (I-2), and the third two-position two-port electromagnetic valve (II-3) with a flow rate of 1,050 ml/min, and is finally discharged into to outdoor. This is also the second sub-stage of the precise clean air calibration, lasting 7 s.

Figure 4:
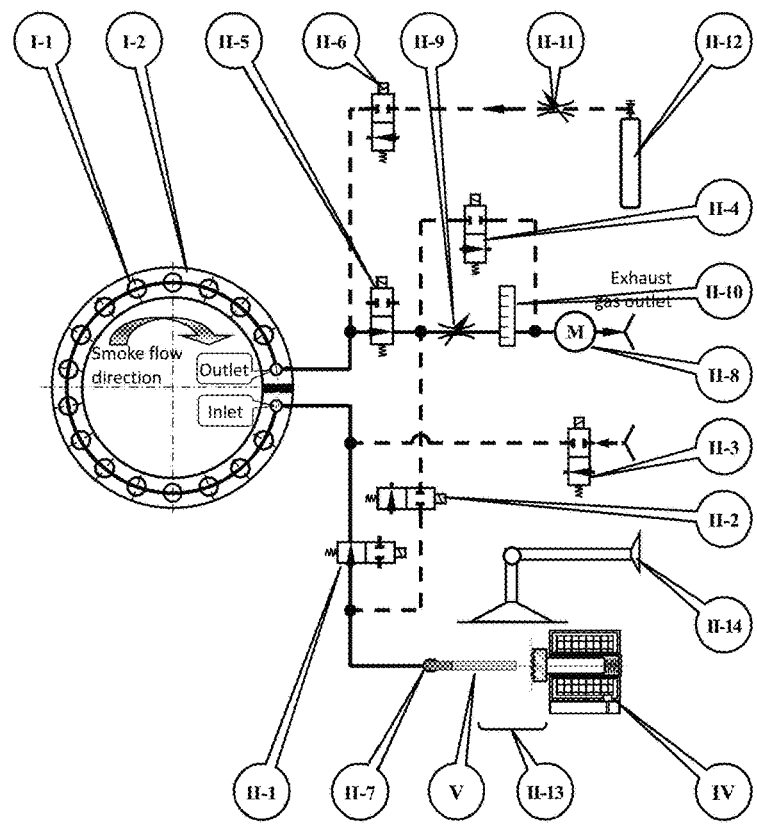
FIG. 4 illustrates a schematic diagram of on-off states of multiple two-position two-port electromagnetic valves and gas paths (under a second smoke puff stage) according to the present disclosure named a sensory quality evaluation method for tobacco and tobacco products using an electronic nose instrument.

FIG. 4 is a schematic diagram illustrating the on-off state of the two-position two-port electromagnetic valves and the gas paths when the electronic nose instrument sucks the second smoke gas. In this state, the first two-position two-port electromagnetic valve (II-1) and the fifth two-position two-port electromagnetic valve (II-5) are turned on, and the other four two-position two-port electromagnetic valves are disconnected. The cigarette smoke gas sequentially flows through the first two-position two-port electromagnetic valve (II-1), the gas sensor array (I-1) as well as the annular working chamber (I-2), the fifth two-position two-port electromagnetic valve (II-5), and the first throttle valve (II-9), the flowmeter (II-10), and is eventually discharged to outdoor for 2 s, which is equivalent to collecting 35 ml smoke gas. At this time, the ignition coil (IV-1) of the automatic ignition device (IV) is cut off, the electromagnetic coil (IV-4) is energized and the valve core (IV-3) is forced to move 9 mm horizontally to the right, which makes the ignition coil (IV-1) out of contact with the tested cigarette sample (V).

During the flow of the second smoke gas, the gas sensor array (I-1) produces a sensitive response. For a specified $p^{th}$ tobacco and tobacco product sample, the steady-state maximum value $U_{pi}(max)$ of the voltage response curve of a gas sensor i is extracted as the feature component $x_{pi}'$ (also referred to as the maximum steady-state voltage response $x_{pi}'$), i.e., $x_{pi}'=U_{pi}(max)$. The gas sensor array (I-1) composed of 16 gas sensors thus produces a 16-dimensional voltage response vector $x_p'=(x_{p1}', x_{p2}', \ldots, x_{pi}', \ldots, x_{p16}')^T \in R^{16}$. This 16-dimensional steady-state maximum voltage response vector is the basis for the tobacco electronic nose instrument to identify tobacco and tobacco products and estimate their sensory quality index scores.

Figure 5:
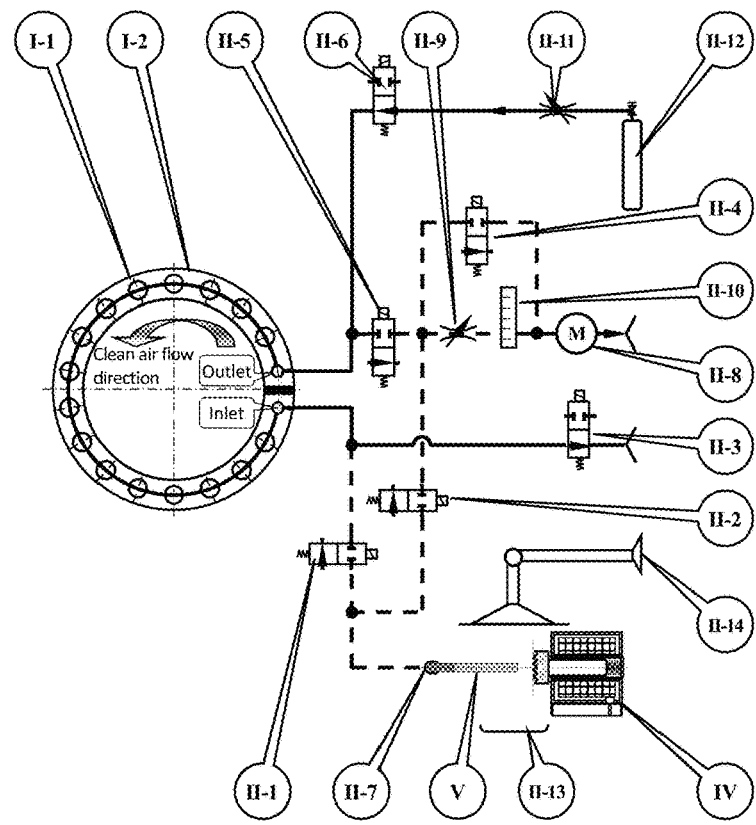
FIG. 5 illustrates a schematic diagram of on-off states of multiple two-position two-port electromagnetic valves and gas paths (a precise clean air calibration stage, a sample insertion stage and a smoldering/self-sustaining combustion stage) according to the present disclosure named a sensory quality evaluation method for tobacco and tobacco products using an electronic nose instrument.

FIG. 5 is a schematic diagram illustrating that the tested cigarette sample (V) inserts into the cigarette holder (II-7) and are in the smoldering/self-sustaining combustion stage, and the on-off state of the two-position two-port electromagnetic valves and the gas paths. In this stage, the third two-position two-port electromagnetic valve (II-3) and the sixth two-position two-port electromagnetic valve (II-6) are turned on, while the other four two-position two-port electromagnetic valves are disconnected. The cigarette insertion operation is manual, lasting 15 s. The time length of the cigarette smoldering/self-sustaining combustion stage is (18+2) s and adjustable. Here, "+2" s refers to the balance time.

During this period, the gas sensor array (I-1) is in the precise clean air calibration stage. The third two-position two-port electromagnetic valve (II-3) and the sixth two-position two-port electromagnetic valve (II-6) are connected. The clean air sequentially flows through the second throttle valve (II-11), the sixth two-position two-port electromagnetic valve (II-6), the gas sensor array (I-1) as well as the annular working chamber (I-2) and the third two-position two-port electromagnetic valve (II-3) with a flow rate of 1,050 ml/min, and is finally discharged to outdoor. This stage is called the first sub-stage of the precise clean air calibration, which lasts 15+18=33 s. This time stage, together with the ignition of the tested cigarette sample (V) in FIG. 3 and the first cigarette suction in the automatic smoke sampling system (II), makes the total time length for the precise clean air calibration stage to be 40 s.

Figure 6:
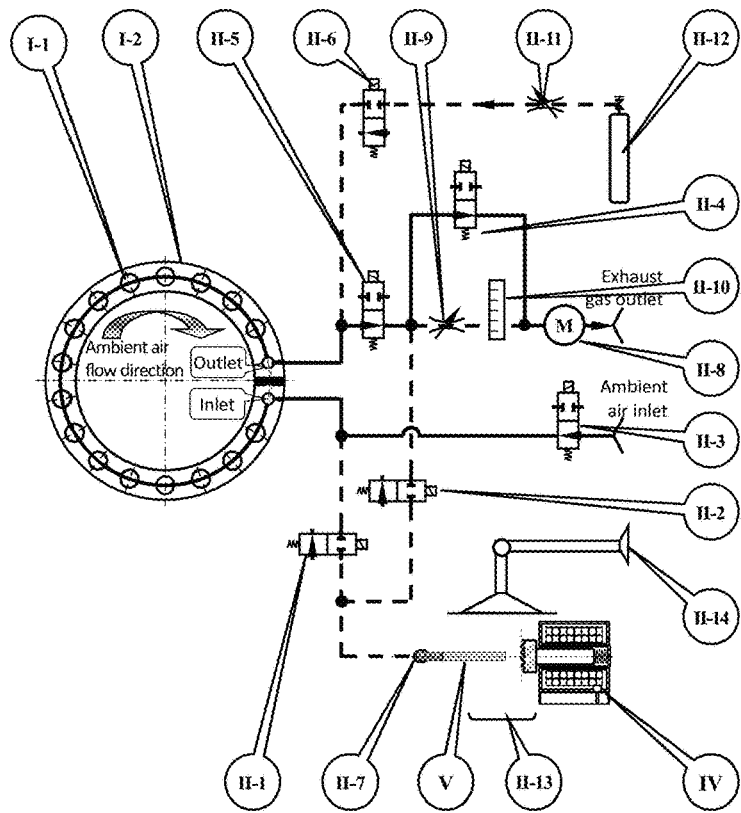
FIG. 6 illustrates a schematic diagram of on-off states of multiple two-position two-port electromagnetic valves and gas paths (an ambient air flushing stage, a residual cigarette butt removal stage) according to the present disclosure named a sensory quality evaluation method for tobacco and tobacco products using an electronic nose instrument.

FIG. 6 is a schematic diagram illustrating the on-off state of the two-position two-port electromagnetic valves and gas paths during removal of the residual cigarette butt. At this stage, the third two-position two-port electromagnetic valve (II-3), the fourth two-position two-port electromagnetic valve (II-4) and the fifth two-position two-port electromagnetic valve (II-5) are turned on, and the other three two-position two-port electromagnetic valves are disconnected. The indoor ambient air sequentially flows through the third two-position two-port electromagnetic valve (II-3), the gas sensor array (I-1) and the annular working chamber (I-2), the fifth two-position two-port electromagnetic valve (II-5) and the fourth two-position two-port electromagnetic valve (II-4) with a flow rate of 6,500 ml/min, and is finally discharged into the outdoor atmosphere. The manual operation time of removing the residual cigarette butt is 15 s (adjustable). This stage is the first sub-stage of the ambient air flushing, which can be regarded as a part of the early recovery stage of the gas sensor array (I-1).

Figure 7:
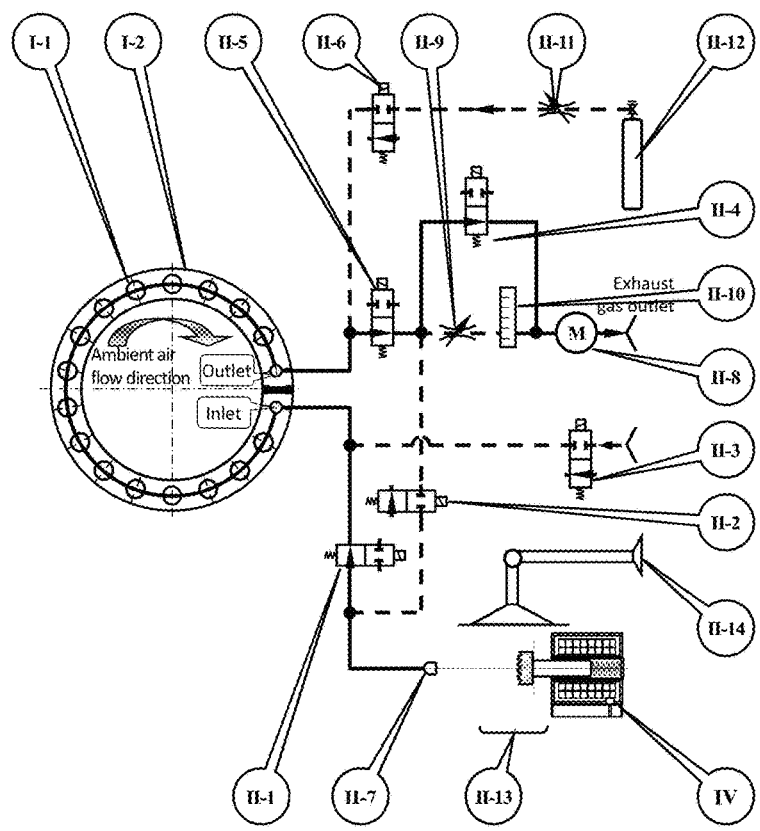
FIG. 7 illustrates a schematic diagram of on-off states multiple two-position two-port electromagnetic valves and gas paths (an early recovery stage of the gas sensor) according to the present disclosure named a sensory quality evaluation method for tobacco and tobacco products using an electronic nose instrument.

FIG. 7 is a schematic diagram illustrating the on-off state of the two-position two-port electromagnetic valves and gas paths after the residual cigarette butt removal. At this stage, the first two-position two-port electromagnetic valve (II-1), the fourth two-position two-port electromagnetic valve (II-4) and the fifth two-position two-port electromagnetic valve (II-5) are turned on, and the other three two-position two-port electromagnetic valves are disconnected. The ambient air sequentially flows through the cigarette holder (II-7), the first two-position two-port electromagnetic valve (II-1), the gas sensor array (I-1) and the annular working chamber (I-2), the fifth two-position two-port electromagnetic valve (II-5), and fourth two-position two-port electromagnetic valve (II-4) with a flow rate of 6,500 ml/min, and is eventually discharged into the outdoor atmosphere.

This stage is the second sub-stage of the ambient air flushing, which lasts 31 s and may be regarded as another part of the early recovery stage of the gas sensor array (I-1). As soon as the second sub-stage of the ambient air flushing ends, a new smoke sampling stage automatically starts, or the operator clicks the "End Detection" button in the screen drop-down menu to end the detection process.

In the smoke sampling and analysis process of the tobacco electronic nose instrument with a period of 300 s, the total time length of the ambient air flushing stage and the early recovery stage of the gas sensor array (I-1) is 300−44=256 s. The purpose of the two stages is: (1) the ambient air with a relatively large flow rate of 6,500 ml/min flushes out the smoke gas molecules adhered to the surfaces of sensitive films of gas sensors, the inner wall of the annular working chamber (I-2) and the gas pipelines, during the second smoking puff stage; (2) take away the heat accumulated during the working hours of gas sensors, so that the gas sensors can primarily restore to their initial states.

Figure 8:
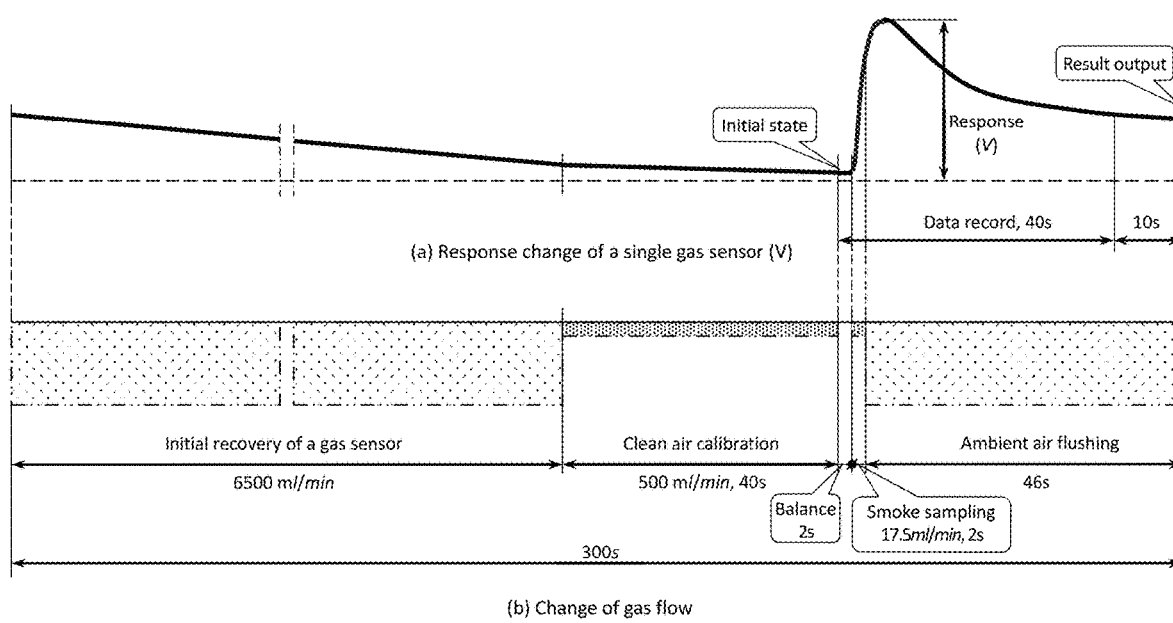
FIG. 8 illustrates a response of a single gas sensor and the change of the gas flow rate and duration in the annular working chamber of the gas sensor array during a smoke sampling period of 300 s according to the present disclosure named a sensory quality evaluation method for tobacco and tobacco products using an electronic nose instrument.

FIG. 8 is a schematic diagram illustrating the voltage response change of a single gas sensor in the tobacco electronic nose instrument and the gas flow rate and duration in the annular working chamber (I-2) of the gas sensor array (I-1) during a smoke sampling period. In a smoke sampling period, the gas flow rates undergoes the three changes of 6,500 ml/min, 1,050 ml/min and 0 (balance); and the gas types goes through the three changes of an ambient air initial flushing, a precise clean air calibration and cigarette smoke sampling. In the balance stage, all six two-position two-port electromagnetic valves are disconnected. There is no gas flow in the gas sensor array (I-1) and the annular working chamber (I-2).

The smoke sampling period of a tested cigarette sample (V) is 300 s. From the beginning of the balance stage, i.e. the $250^{th}$ second of the smoke sampling period, the computer control and data analysis system (III) records the transient voltage response data of the gas sensor array for 40 s, including 2 s of the balance stage, 2 s of the sampling stage of the second smoke gas and 36 s of the first half of the ambient air flushing stage. The voltage responses of the gas sensor array (I-1) to the smoke, i.e., the sampling data, are saved in a text file. Within 40 s of data recording, the steady-state maximum voltage value of the response curve of the gas sensor i to the smoke of the $p^{th}$ cigarette sample is extracted as the feature component $x_{pi}'$. Therefore, the response of the gas sensor array to the second smoke gas of the $p^{th}$ cigarette sample is obtained, which is called the voltage response pattern $x_p' \in R^{16}$. Within 10 s after the end of the data recording, the computer control and data analysis system (III) gives the brand recognition results of the $p^{th}$ cigarette sample and the score estimation results of the five sensory quality indices such as aroma, harmony, impurity, irritation and aftertaste, based on the pattern $x_p'$.

Why should the sampling flow rate of the cigarette smoke be set at 17.5 ml/s, i.e., 1,050 ml/min, and the sampling time length be set at 2 s. A large number of statistical results indicate that the volume of smoke gas inhaled by a person is 35 ml, with an average time length of 2 s. The China national standard "Routine Analytical Cigarette-Smoking Machine—Definitions and Standard Conditions" GB/T16450-2004 stipulates that the standard puff volume of cigarette smoke is 35 ml, the flow rate is 17.5 ml/s, and the standard single-mouth puff duration is 2.00±0.02 s. The sampling flow rate, volume and duration of the cigarette smoke gas of the present disclosure are consistent with the national standard GB/T16450. For the sake of uniformity, the flow rate of clean air is still set at 1,050 ml/min.

Figure 9:
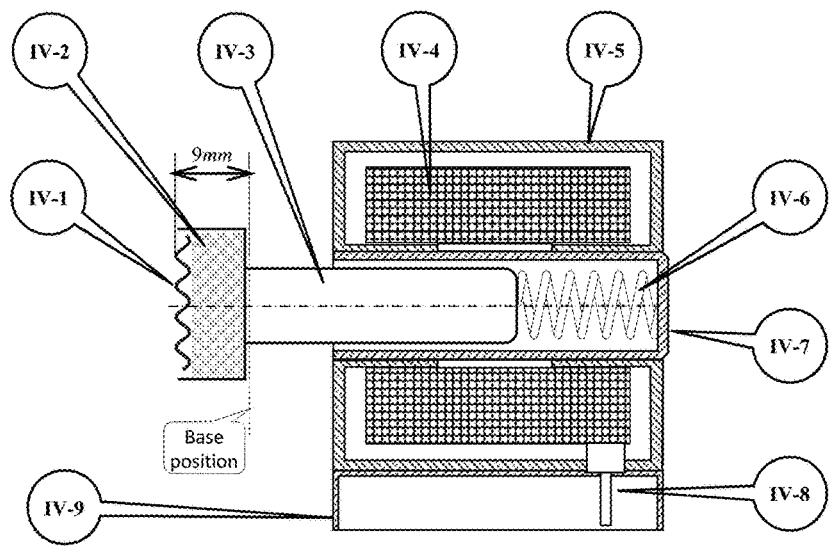
FIG. 9 illustrates a schematic diagram of automatic ignition device (a power-off state of the electromagnetic coil) according to the present disclosure named a sensory quality evaluation method for tobacco and tobacco products using an electronic nose instrument.

FIG. 9 is a schematic diagram illustrating the component units of the automatic ignition device (IV) when the electromagnetic coil (IV-4) is turned off. The automatic ignition device (IV) is located at the right front bottom of the tobacco electronic nose instrument and includes: the ignition coil (IV-1), the cigarette igniter (IV-2), the movable iron core (IV-3), the electromagnetic coil (IV-4), the magnetic permeable iron frame (IV-5), the compression spring (IV-6), the spring seat (IV-7), the cable (IV-8) and the support (IV-9). The working voltage of the ignition coil (IV-1) and the electromagnetic coil (IV-4) is 24V DC, and the maximum working current of the ignition coil is 5A. Starting from the fifth second before sucking the first smoke gas, the ignition coil (IV-1) is powered, and the temperature rises to 380° C. within 5 s, when the electromagnetic coil (IV-4) is energized. At the same time, the electromagnetic coil (IV-4) is cut off. Under the role of the compression spring (IV-6), the ignition coil (IV-1) and the cigarette igniter (IV-2) fixed on the movable iron core (IV-3) move 9 mm horizontally to the left from the reference position, and touch and ignite the tip of the tested cigarette sample (V).

Figure 10:
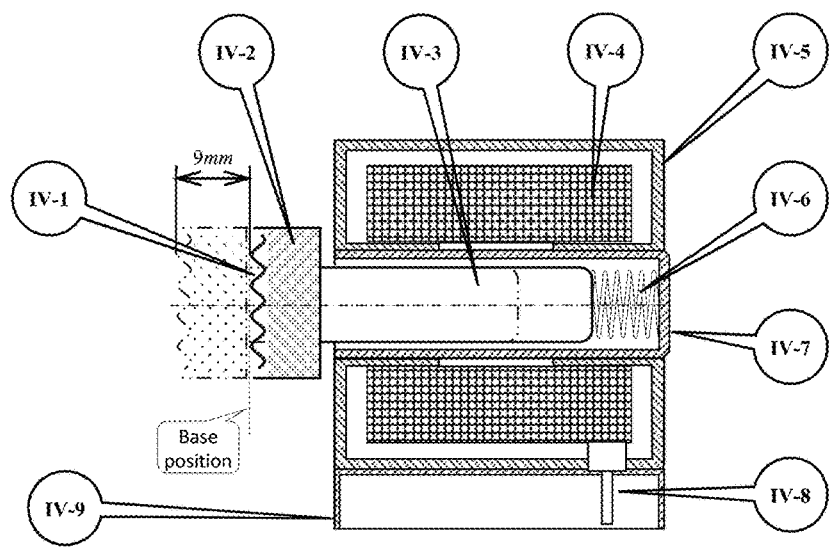
FIG. 10 illustrates a schematic diagram of automatic ignition device (a power-on state of the electromagnetic coil) according to the present disclosure named a sensory quality evaluation method for tobacco and tobacco products using an electronic nose instrument.

FIG. 10 is a schematic diagram illustrating the component units of the automatic ignition device (IV) when the electromagnetic coil (IV-4) is energized. In this state, the electromagnetic coil (IV-4) is turned on and the ignition coil (IV-1) is cut off. Under the force of the electromagnetic coil (IV-4), the compression spring (IV-6) is compressed by 9 mm, and the ignition coil (IV-1) and the cigarette igniter (IV-2) fixed on the movable iron core (IV-3) are restored to the reference position to prepare for the manual insertion of the tested cigarette sample and the manual removal of the residual cigarette butt.

It must be pointed out that as long as the tested cigarette sample (V) is not inserted into the cigarette holder (II-7), the ignition coil (IV-1) and the electromagnetic coil (IV-4) are always in the power-off state. Under the role of the compression spring (IV-6), the ignition coil (IV-1) and the cigarette igniter (IV-2) are both in the position of 9 mm horizontal left shift of the reference position. During a smoke sampling period, the electrification duration of the electromagnetic coil (IV-4) is: 15 s of manual insertion of the tested cigarette sample (V) into the cigarette holder (II-7); is (that is the $2^{nd}$ second) of the first smoke puff stage; 18 s of the smoldering/self-sustaining combustion stage of the tested cigarette sample (V); 2 s of the balanced stage; 2 s of the second smoke puff stage; and 15 s of the residual cigarette butt removal stage. The ignition coil (IV-1) is energized during the first 6 s of the ignition of the tested cigarette sample (V) and the smoke automatic injection system (II) during the first smoke puff stage, and the power was cut off for the rest of the time.

FIG. 11 is a schematic diagram illustrating the on-off relationship between six two-position two-port electromagnetic valves, the ignition coil (IV-1) and the electromagnetic coil (IV-4) in a smoke sampling period. FIG. 11(a) shows that the first two-position two-port electromagnetic valve (II-1) is electrified in the first 210 s and the last 31 s except for the second smoke puff period of 2 s. It is convenient for the ambient air to flush the smoke molecules on the surface of the cigarette holder (II-7), the sensitive film of the gas sensor array and the inner wall of the pipes for a longer time.

FIGS. 11(b) and (f) illustrate that the second two-position two-port electromagnetic valve (II-2) only controls a puff of the first smoke gas, and the sixth two-position two-port electromagnetic valve (II-6) only controls the opening and closing of the clean air. The roles of the second and the sixth two-position two-port electromagnetic valves are relatively single. According to FIG. 11(c), the third two-position two-port electromagnetic valve (II-3) is conductive in 40 s of the precise clean air calibration stage and 15 s after the end of the second smoke puff stage, but the flow direction and flow rate of the gas flow are different. During the 40 s of the previous stage, the clean air flows through the third two-position two-port electromagnetic valve (II-3) after flowing through the annular working chamber (I-2) with a flow rate of 1,050 ml/min, and then is discharged to outdoor. During the 15 s of the next stage, the indoor ambient air with a flow rate of 6,500 ml/min flows into the annular working chamber (I-2) from the third two-position two-port electromagnetic valve (II-3), and then is discharged to outdoor through the fourth two-position two-port electromagnetic valve (II-4) and the fifth two-position two-port electromagnetic valve (II-5).

FIG. 11(d) shows that the fourth two-position two-port electromagnetic valve (II-4) is disconnected in three stages: the precise clean air calibration stage, the balance stage and the second smoke puff stage, thus forcing the first and the second smoke gases to flow through the throttle valve (II-9) with a flow rate of 1,050 ml/min. The fourth two-position two-port electromagnetic valve (II-4) mainly controls the gas flow change between 6,500 ml/min and 1,050 ml/min. Comparing FIG. 11(e) with FIG. 11(d), the states of the fourth two-position two-port electromagnetic valve (II-4) and the fifth two-position two-port electromagnetic valve (II-5) are inconsistent only in the second smoke puff stage. During this period, the fifth two-position two-port electromagnetic valve (II-5) is turned on and the fourth two-position two-port electromagnetic valve (II-4) is disconnected, forcing the second smoke gas to flow through the throttle valve (II-9) with a flow rate of 1,050 ml/min.

FIG. 11(g) shows that the ignition coil (IV-1) is energized only for a total of 6 s before the ignition and during the first smoke puff, and is disconnected for the rest of the smoke sampling period. FIG. 11(h) shows that the electromagnetic coil (IV-4) is energized 53 s in a smoke sampling period, including 15 s during the insertion of a cigarette sample, the $2^{nd}$ second of the first smoke puff, the 18 s of smoldering/self-sustaining combustion, the 2 s of the balance, the 2 s of the second smoke puff, and the 15 s during the residual cigarette butt removal. The ignition coil (IV-1) is disconnected in the remaining time of the smoke sampling period.

Figure 12:
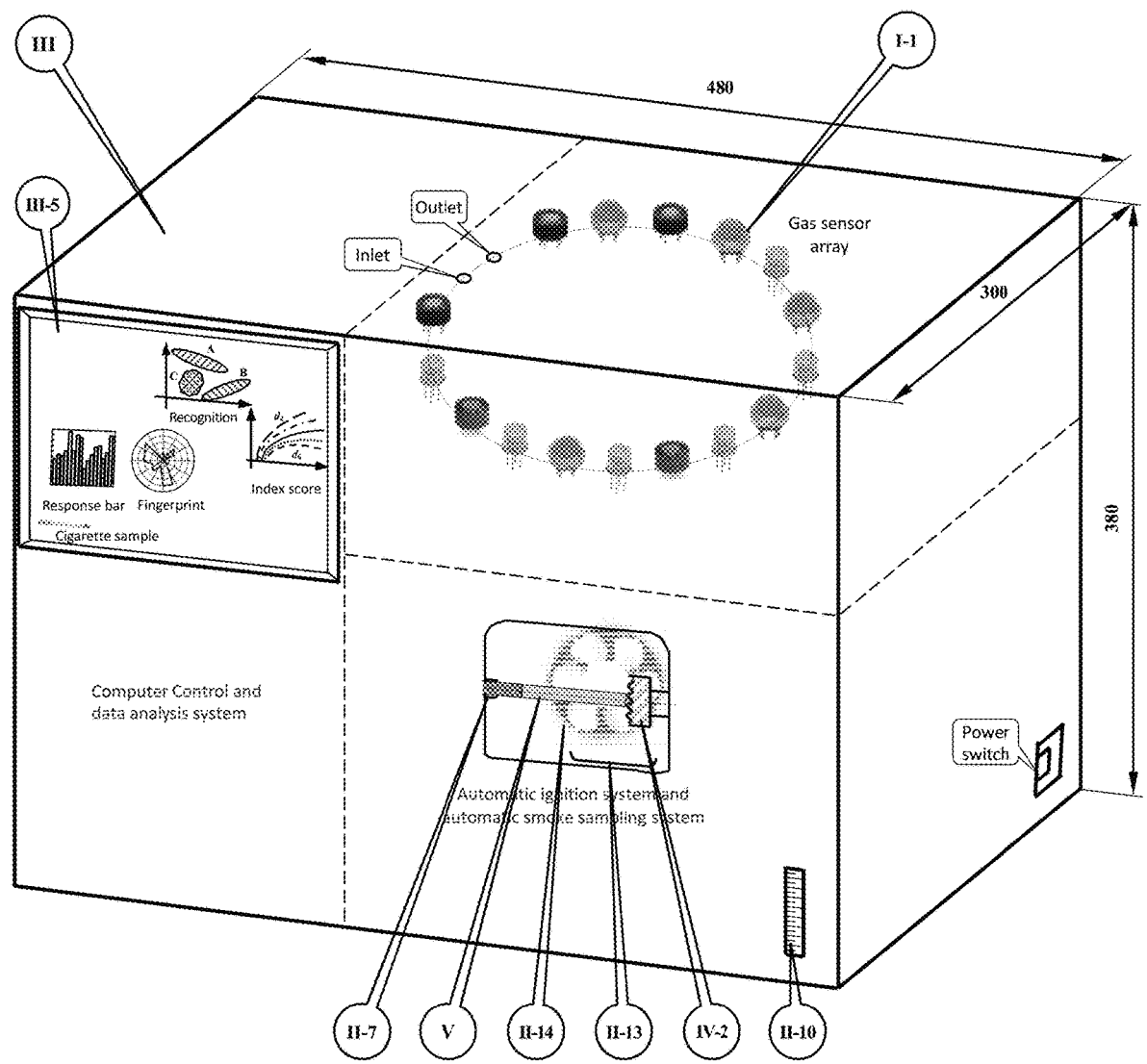
FIG. 12 illustrates a stereoscopic appearance sketch of the tobacco electronic nose instrument according to the present disclosure named a sensory quality evaluation method for tobacco and tobacco products using an electronic nose instrument.

FIG. 12 is a three-dimensional spatial diagram of the tobacco electronic nose instrument. As can be seen from the figure, the gas sensor array module (I) is located at the upper right part; the computer control and data analysis system (III) is located on the left side; the smoke automatic sampling system (II) and the automatic ignition device (IV) are located at the lower right part.

Figure 13:
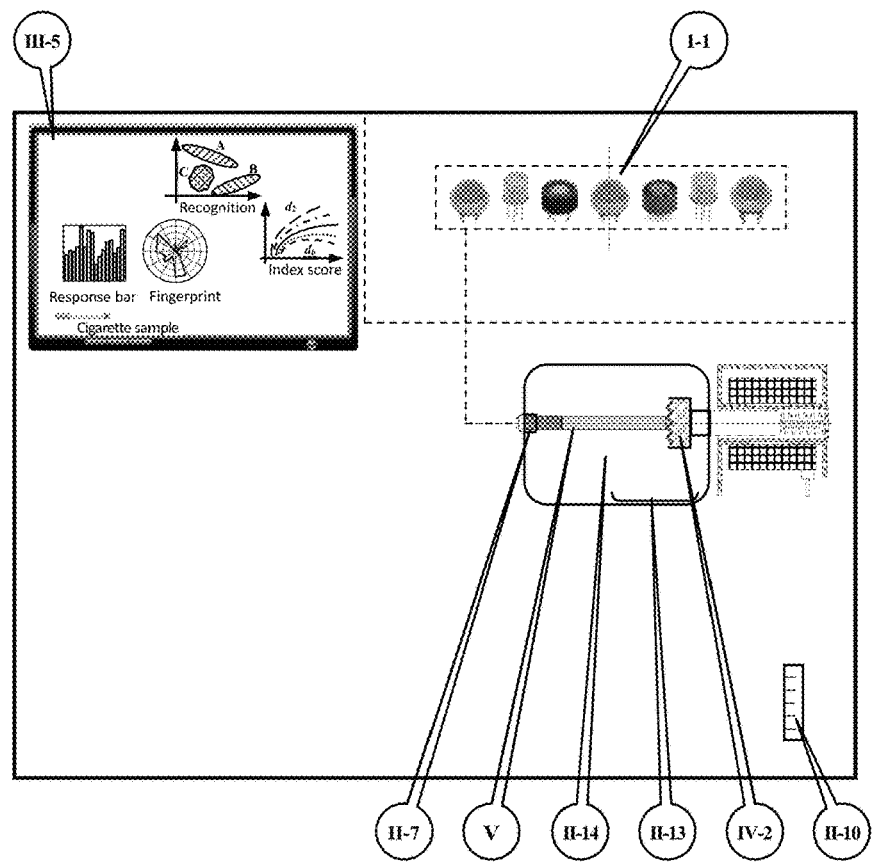
FIG. 13 illustrates a frontal schematic diagram of the tobacco electronic nose instrument according to the present disclosure named a sensory quality evaluation method for tobacco and tobacco products using an electronic nose instrument.

FIG. 13 is a front view of the tobacco electronic nose instrument. According to this figure, the external visible parts are the monitor (III-5) of the computer control and data analysis system (III), the cigarette holder (II-7) of the smoke automatic sampling system (II), the exhaust fan of the overflow smoke gas discharge device (II-14), the cigarette igniter (IV-2) of the automatic ignition device (IV), and the tested cigarette sample (V).

Figure 14:
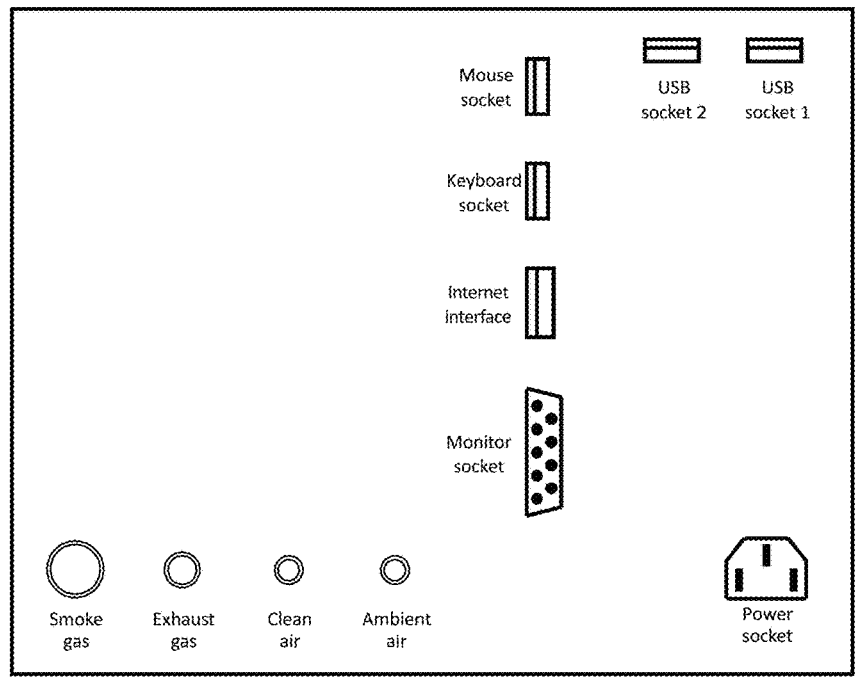
FIG. 14 illustrates a back schematic diagram of the tobacco electronic nose instrument according to the present disclosure named a sensory quality evaluation method for tobacco and tobacco products using an electronic nose instrument.

FIG. 14 is the schematic diagram on the back of the tobacco electronic nose instrument. The electronic nose instrument is equipped with an interface for an external monitor, two USB interfaces, a mouse interface, a keyboard interface, an Internet interface, an environmental air entrance a clean air entrance, and a smoke gas outlet from the automatic smoke gas injection system (II). The smoke gas is directly discharged from the overflow smoke gas discharge device (II-14). Users can easily plug in the external devices such as a large-screen monitor, a keyboard and a mice for data transmission, switching and remote Internet transmission.

FIG. 15 is the first-order partial derivative curve and the ratio change curve of the modified Sigmoid activation function $f(\varphi)=3/(1+\exp(-\varphi/3))$ and the standard Sigmoid activation function $f_0(\varphi)=1/(1+\exp(-\varphi))$ in the interval $\varphi\in[-10, 10]$. FIG. 15(a) is the first-order partial derivative curves $\partial f/\partial \varphi$ and $\partial f_0/\partial \varphi$ of the two activation functions in this interval. The real line is the first-order partial derivative curve $\partial f/\partial \varphi$ of the modified activation function $f(\varphi)$, and the dashed line is the first-order partial derivative curve $\partial f_0/\partial \varphi$ of the standard Sigmoid activation function $f_0(\varphi)$. FIG. 15(b) is the ratio curve $\rho=\partial f/\partial \varphi : \partial f_0/\partial \varphi$ of two first-order partial derivatives of the modified to the standard sigmoid activation functions. Why is the modified sigmoid activation function $f(\varphi)$ employed? Because the single-hidden-layer neural networks adopt the error back-propagation learning algorithm; and the greater the partial derivatives (first-order gradients) of error-squared sums between the actual and the expected outputs, the faster the learning speeds, if without oscillation.

FIG. 15 shows that the first-order gradient of the modified Sigmoid activation function $f(\varphi)$ is much larger than that of the standard Sigmoid activation function $f_0(\varphi)$. When $\varphi=\pm 10.0$, the first-order gradient ratio between the modified and the standard Sigmoid activation function reaches $\rho=732.63$. Corresponding to this, the input component is transformed to the range of [0, 6]. This approach considers that the mean component values of the training set X are around 3.0 regardless of the sample distribution. Neural networks using the standard Sigmoid activation function $f_0(\varphi)$ generally transform datasets to the range of [0, 1], which means that the actual default means of components are about 0.5. In contrast, the advantage of transforming the input components into the range of [0, 6] is that the sample margin and class margin are enlarged six times as big as the original [0, 1], which is helpful to accelerating the learning speed, improving the learning accuracies and generalization abilities of neural networks without oscillation.

The single-output neural network $\overline{\omega}_{jk}$ for identifying two cigarette brands $\{\omega_j, \omega_k\}$ has m=16 input nodes, $s_1$=8 hidden nodes and 1 output node. All input components are proportional to the [0, 6] range, and the target output is encoded by $\{0.0, 3.0\}$ and the activation functions of all hidden nodes and output nodes are $f(\varphi)$. The error back-propagation algorithm is used to train the single-output neural network, and the learning rate is $\eta_{jk}=10/N_{jk}=0.17$.

This present disclosure adopts the OAO task decomposition method. The original tobacco training set X with n brands is decomposed into $C_n^2=n(n-1)/2$ binary-class sub-problems. The n(n−1)/2 sub-problems are studied and solved one by one by n(n−1)/2 single-output neural networks, thus constituting the first level of cascade modular neural network model. Table 3 gives a list of n(n−1)/2 single-output neural networks $\{\overline{\omega}_{jk}\}$ (j, k=1, 2, . . . , n, j≠k).

TABLE 3

The list of n(n − 1)/2 single-output neural networks studying to identify n tobaccos products

| Brand number | 1 | 2 | ... | j − 1 | J | j + 1 | ... | n − 1 | N |
|---|---|---|---|---|---|---|---|---|---|
| 1 | — | $\overline{\omega}_{12}$ | ... | $\overline{\omega}_{1(j-1)}$ | $\overline{\omega}_{1j}$ | $\overline{\omega}_{1(j+1)}$ | ... | $\overline{\omega}_{1(n-1)}$ | $\overline{\omega}_{1n}$ |
| 2 | — | — | ... | $\overline{\omega}_{2(j-1)}$ | $\overline{\omega}_{2j}$ | $\overline{\omega}_{2(j+1)}$ | ... | $\overline{\omega}_{2(n-1)}$ | $\overline{\omega}_{2n}$ |
| ... | | | | | | | | | |
| j − 1 | — | — | — | — | ... | $\overline{\omega}_{(j-1)(j+1)}$ | ... | $\overline{\omega}_{(j-1)(n-1)}$ | $\overline{\omega}_{(j-1)n}$ |
| j | — | — | — | — | — | $\overline{\omega}_{j(j+1)}$ | ... | $\overline{\omega}_{j(n-1)}$ | $\overline{\omega}_{jn}$ |
| j + 1 | — | — | — | — | — | — | ... | $\overline{\omega}_{(j+1)(n-1)}$ | $\overline{\omega}_{(j+1)n}$ |
| ... | | | | | | | | ... | ... |
| n − 1 | — | — | — | — | — | — | — | — | $\overline{\omega}_{(n-1)n}$ |
| n | | | | | | | | | |

TABLE 4

The list of n(n − 1)/2 vote recognition groups to determine the brand names of n tobaccos products

| Brand number | 1 | 2 | ... | j − 1 | j | j + 1 | ... n − 1 | n | Group | No. votes |
|---|---|---|---|---|---|---|---|---|---|---|
| 1 | — | $\overline{\omega}_{12}$ | ... | $\overline{\omega}_{1(j-1)}$ | $\overline{\omega}_{1j}$ | $\overline{\omega}_{1(j+1)}$ | ... $\overline{\omega}_{1(n-1)}$ | $\overline{\omega}_{1n}$ | $\Omega_1$ | $\Delta_1$ |
| 2 | $\overline{\omega}_{12}$ | — | ... | $\overline{\omega}_{2(j-1)}$ | $\overline{\omega}_{2j}$ | $\overline{\omega}_{2(j+1)}$ | ... $\overline{\omega}_{2(n-1)}$ | $\overline{\omega}_{2n}$ | $\Omega_2$ | $\Delta_2$ |
| ... | ... | ... | ... | ... | ... | ... | ... ... | ... | ... | ... |
| j − 1 | $\overline{\omega}_{1(j-1)}$ | $\overline{\omega}_{2(j-1)}$ | ... | — | $\overline{\omega}_{(j-1)j}$ | $\overline{\omega}_{(j-1)(j+1)}$ | ... $\overline{\omega}_{(j-1)(n-1)}$ | $\overline{\omega}_{(j-1)n}$ | $\Omega_{j-1}$ | $\Delta_{j-1}$ |
| j | $\overline{\omega}_{1j}$ | $\overline{\omega}_{2j}$ | ... | $\overline{\omega}_{(j-1)j}$ | — | $\overline{\omega}_{j(j+1)}$ | ... $\overline{\omega}_{j(n-1)}$ | $\overline{\omega}_{jn}$ | $\Omega_j$ | $\Delta_j$ |
| j + 1 | $\overline{\omega}_{1(j+1)}$ | $\overline{\omega}_{2(j+1)}$ | ... | $\overline{\omega}_{(j-1)(j+1)}$ | $\overline{\omega}_{j(j+1)}$ | — | ... $\overline{\omega}_{(j+1)(n-1)}$ | $\overline{\omega}_{(j+1)n}$ | $\Omega_{j+1}$ | $\Delta_{j+1}$ |
| ... | ... | ... | ... | ... | ... | ... | ... — | ... | ... | ... |

TABLE 4-continued

The list of n(n − 1)/2 vote recognition groups
to determine the brand names of n tobaccos products

| Brand number | 1 | 2 | ... | j − 1 | j | j + 1 | ... n − 1 | n | Group | No. votes |
|---|---|---|---|---|---|---|---|---|---|---|
| n − 1 | $\overline{\omega}_{1(n-1)}$ | $\overline{\omega}_{2(n-1)}$ | ... | $\overline{\omega}_{(j-1)(n-1)}$ | $\overline{\omega}_{j(n-1)}$ | $\overline{\omega}_{(j+1)(n-1)}$ | ... — | $\overline{\omega}_{(n-1)n}$ | $\Omega_{(n-1)}$ | $\Delta_{n-1}$ |
| n | $\overline{\omega}_{1n}$ | $\overline{\omega}_{2n}$ | ... | $\overline{\omega}_{(j-1)n}$ | $\overline{\omega}_{jn}$ | $\overline{\omega}_{(j+1)n}$ | ... $\overline{\omega}_{(n-1)n}$ | — | $\Omega_n$ | $\Delta_n$ |

In order to determine the brand of the undetermined cigarette pattern x, the n(n−1)/2 single-output neural networks in the first-level of the cascade modular neural network model use the majority vote rules for decision-making. Table 4 gives a grouping list of n(n−1)/2 single-output neural networks for vote to determine which brand of tobacco and tobacco products the undetermined cigarette pattern x belongs to. Table 4 is principally diagonal symmetric. A single-output neural network must participate in two vote recognition groups. For example, the single-output neural network $\overline{\omega}_{jk}$ not only participates in the vote of the vote recognition group $\Omega_j$, but also participates in the vote of the vote recognition group $\Omega_k$.

In the present disclosure—a sensory quality evaluation method for tobacco and tobacco products using an electronic nose instrument, FIG. 16 gives the vote occasion of n(n−1)/2 single-output neural networks by being divided into n vote recognition groups with (n−1) members in each group, when determining the brand of an undetermined cigarette pattern x.

Figure 17:
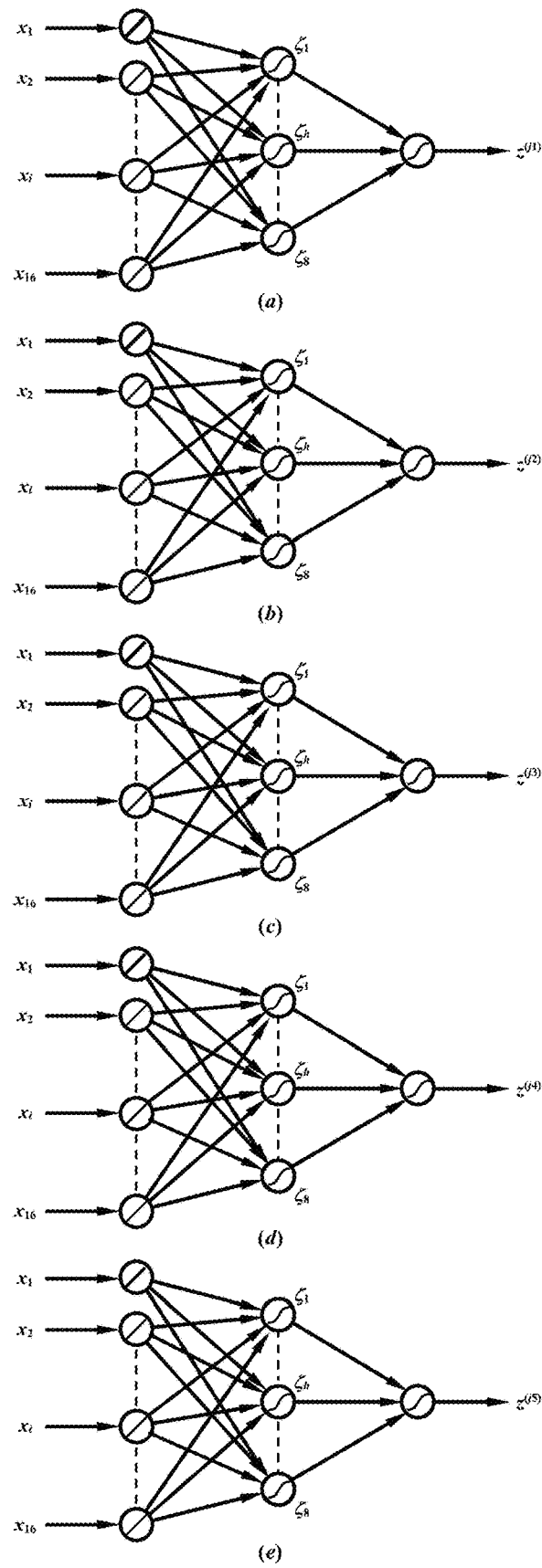
FIG. 17 illustrates a schematic diagram of sensory quality index score estimation group $\Lambda_j$ consisting of five single-output neural networks according to the present disclosure named a sensory quality evaluation method for tobacco and tobacco products using an electronic nose instrument.

There are n score estimation groups which correspond to the vote recognition groups, one by one. Each score estimation group includes five single-output neural networks. In the present disclosure—a sensory quality evaluation method for tobacco and tobacco products using an electronic nose instrument, FIG. 17 shows the sensory quality index score estimation group $\Lambda_j$ includes five single-output neural networks. The five members perform the score estimation of the five sensory quality indices, namely, aroma, harmony, impurity, irritation and aftertaste, for cigarette samples belonging to the brand $\omega_j$. The structure of each single-output neural network is m=16 input nodes, $s_2$=8 hidden nodes, and 1 output node. All input components are converted to the range of [0, 6], and the target output is encoded by {0.0, 3.0}. All hidden nodes and output nodes are with the modified Sigmoid activation functions $f(\varphi)=3/(1+\exp(-\varphi/3))$. The scale of the target outputs corresponding to the sensory quality index score of the brand $\omega_j$ is changed to the range of [0.15, 2.85]. The learning algorithm is the error back-propagation algorithm, and the learning factor is $\eta_j$=0.17.

Figure 18:
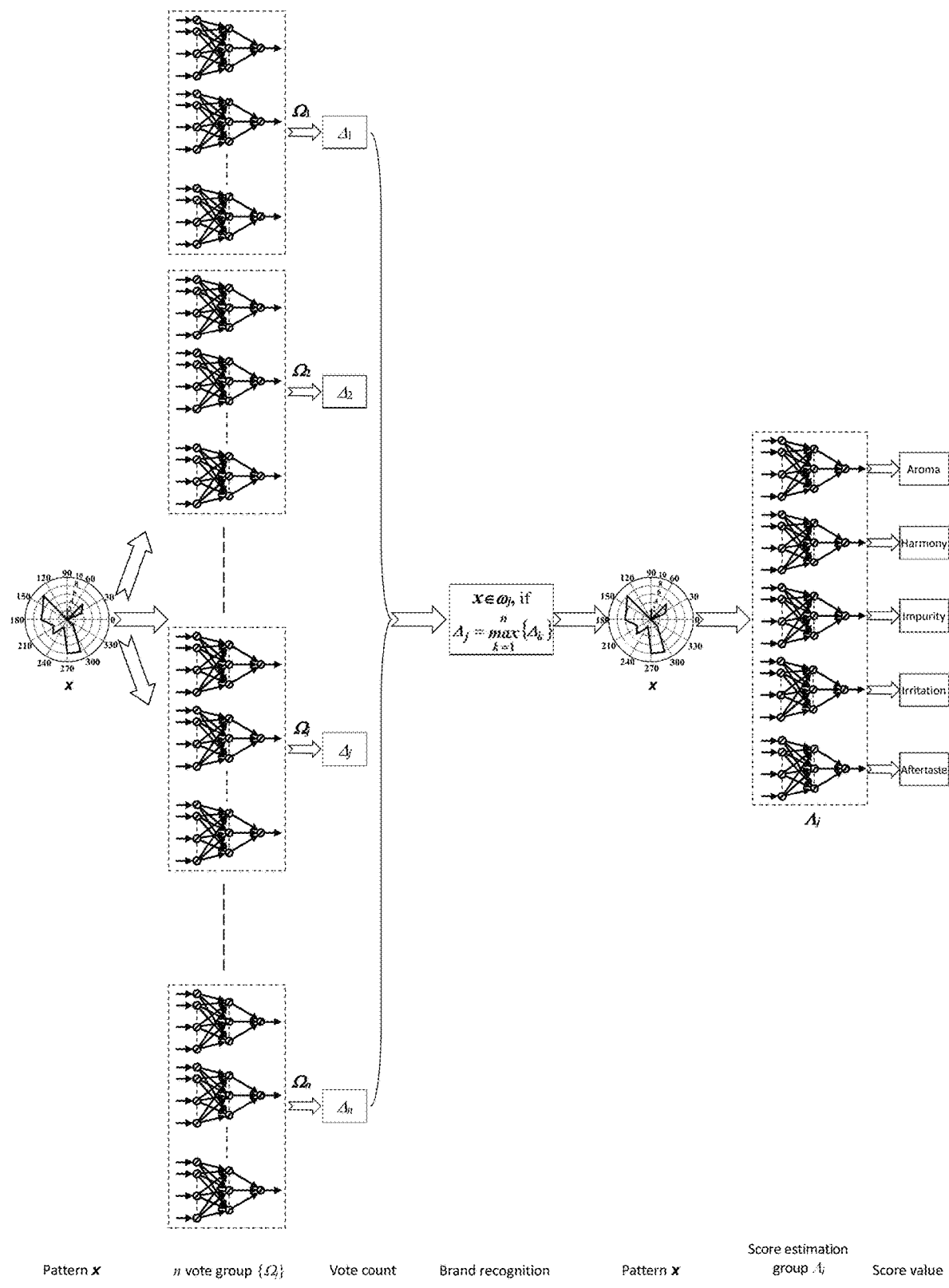
FIG. 18 illustrates a decision-making process diagram of cascade modular neural network model for simultaneous recognition and sensory quality index score estimation of a tobacco and tobacco product sample according to the present disclosure named a sensory quality evaluation method for tobacco and tobacco products using an electronic nose instrument.

FIG. 18 is a schematic diagram illustrating the decision-making process of a cascade modular neural network model for simultaneous (1) recognition and (2) sensory quality index score estimation for a tobacco and tobacco product sample. When the undetermined cigarette pattern x is identified for the ownership of brand, origin and authenticity, all n(n−1)/2 single-output neural networks in the first level of the cascade modular neural network model participate in the whole process and are divided into n vote recognition groups, each vote recognition group has (n−1) members, and a single output neural network participates in two vote recognition groups. The majority vote rules are used in the n vote recognition groups, and the vote recognition group with the highest number of votes wins. When the number of votes in two or more vote recognition groups are equal and the maximum, the decision rule is that the undetermined cigarette pattern x does not belong to any existing brand. When performing the sensory quality index score estimation of the undetermined cigarette pattern x, in the 5n single-output neural networks of the second level, only five single-output neural networks in the score estimation group corresponding to the winning vote recognition group take part in performing the score estimation of the five sensory quality indices, namely, aroma, harmony, impurity, irritation and aftertaste.

What is claimed is:

1. A sensory quality evaluation method for tobacco and tobacco products using an electronic nose instrument, wherein the electronic nose instrument comprising:

a gas sensor array module, an automatic smoke sampling system, a computer control and data analysis system, and an automatic ignition device, so as to realize a sensory quality index score estimation of the tobaccos and tobacco products;

wherein the gas sensor array module comprises 16 $SnO_2$ semiconductor gas sensors, which are evenly distributed in a sealed chamber having a middle diameter of ϕ140 mm and a cross-section size of 20 mm×16 mm and forms an annular working chamber of a gas sensor array; the annular working chamber is disposed in a thermostatic room of 55±0.1° C. and is arranged on a top right of the electronic nose instrument;

the automatic smoke sampling system comprises a cigarette holder, a miniature vacuum pump, a first two-position two-port electromagnetic valve, a second two-position two-port electromagnetic valve, a third two-position two-port electromagnetic valve, a fourth two-position two-port electromagnetic valve, a fifth two-position two-port electromagnetic valve, a sixth two-position two-port electromagnetic valve, a first throttle valve, a second throttle valve, a flowmeter, gas pipelines and an overflow smoke gas discharge device; and the automatic smoke sampling system is disposed on a lower right of the electronic nose instrument;

the automatic ignition device comprises an ignition coil, a cigarette igniter head, a movable iron core, an electromagnetic coil, a magnetic permeable iron frame, a compression spring, a spring seat, a cable, and a support; the automatic ignition device is disposed on a front right bottom of the electronic nose instrument;

the computer control and data analysis system comprises a computer motherboard, a data acquisition card, a precision linear and switching power module, a drive and control circuit module, a hard disk, an internet card, a video card, and a monitor; and the computer control and data analysis system is arranged on a left side of the electronic nose instrument;

wherein the automatic smoke sampling system is configured to perform a smoke sampling period of 5 minutes for a tobacco and tobacco product sample; and the gas sensor array is configured to flow through following five stages according to a type of gases: an early recovery stage of 210 seconds, a precise clean air calibration stage of 40 seconds, a balance stage of 2 seconds, a second smoke puff stage of 2 seconds, and an ambient air flushing stage of 46 seconds;

wherein the method comprises:

during a smoke sampling stage, under a computer control, horizontally moving, by the ignition coil in the automatic ignition device, 9 mm to a left and igniting a cigarette sample at 380° C.; sucking, by the miniature vacuum pump in automatic smoke sampling system, a second smoke gas with a flow rate of 17.5 ml/sec, so as to make the second smoke gas flow through the annular working chamber and sweep over surfaces of sensitive films of the gas sensors for a duration of 2 seconds, so that the gas sensor array produces a sensitive response; from beginning of a balance stage, beginning to sequentially record, by the computer control and data analysis system, voltage response data of the gas sensor array generated in three stages: the balance stage of 2 seconds, the second smoke puff stage of 2 seconds and an ambient air flushing stage of 36 seconds, with a total data recording duration of 40 seconds; in another durations of the smoke sampling period except for 40 seconds, not recording, by the computer control and data analysis system, voltage response data;

within the total data recording duration of 40 seconds, generating, by the gas sensor array comprised by 16 gas sensors, a 16-dimensional voltage response vector when a steady-state maximum voltage value of a response curve of a single gas sensor to the second smoke gas is extracted as a feature component; within 10 seconds after an end of the total data recording duration, performing, by the computer control and data analysis system and according to the 16-dimensional voltage response vector, a recognition of brand, origin of manufacture, and authenticity of tobacco and tobacco products and performing a score estimation of five sensory quality indices: aroma, harmony, impurity, irritation and aftertaste;

performing, by the computer control and data analysis system, a recognition of tobacco and tobacco product samples, and the sensory quality index score estimation of the tobacco and tobacco product samples by using to a cascade modular neural network model; wherein a first level of the cascade modular neural network model comprises n(n−1)/2 single-output neural networks arranged in parallel, forming n vote recognition groups which identifies n kinds of tobacco and tobacco products, wherein the recognition comprises recognitions of brand, origin of manufacture, and authenticity; wherein a second level of the cascade modular network neural model comprises n×5 single-output neural networks, the n×5 single-output neural networks are divided into n groups, and each of the n groups comprises 5 single-output neural networks and is used to perform the score estimation of the five sensory quality indices: aroma, harmony, impurity, irritation and aftertaste, for the n kinds of tobacco and tobacco products.

2. The method according to claim 1, wherein the cigarette holder has an angle of 0 to 5 degrees between an axis of the cigarette holder and a horizontal plane; before the cigarette sample is automatic ignited, inserting, by an operator, a butt of the cigarette sample into the cigarette holder at a depth of 9±0.5 mm, an inserting operation lasting 15 seconds; and within 15 seconds after an end of the second smoke puff stage, removing, by the operator, a remaining cigarette butt from the cigarette holder, extinguishing and discarding it, within 15 seconds.

3. The method according to claim 1, wherein the ignition coil of the automatic ignition device operates with a 24V working voltage and a 5A current; axes of the cigarette igniter head, the movable iron core, the electromagnetic coil, the compression spring, and the cigarette holder, are arranged at a same horizontal line; under the computer control, the ignition coil is energized from a fifth second before a first smoke puff action and heated to 380° C. within 5 seconds; meanwhile, the electromagnetic coil powers off, and under an action of the compression spring, the ignition coil on the cigarette ignitor head moves 9 mm horizontally from a reference position to a left and ignite the cigarette sample; after a first smoke is sucked for 1 s, the ignition coil is switched off and the electromagnetic coil is energized; under an action of an electromagnetic force of the electromagnetic coil, the ignition coil disengages from the ignited cigarette sample and returns to a reference position.

4. The method according to claim 1, wherein under a suction action of the miniature vacuum pump, a first smoke gas of the cigarette sample is, for 2 seconds, directly discharged to outdoor after sequentially passing through the second two-position two-port electromagnetic valve, the first throttle valve and the flowmeter with a flow rate of 17.5 ml/s, so that the first smoke gas completely does not pass through the annular working chamber and a 35 ml volume of smoke gas is drawn; then the ignited cigarette sample is smoldered/self-sustaining combustion for 20 seconds.

5. The method according to claim 1, wherein under the suction action of the miniature vacuum pump, the second smoke gas of the cigarette sample is, for 2 seconds, discharged to outdoor after sequentially passing through the first two-position two-port electromagnetic valve, the annular working chamber, the fifth two-position two-port electromagnetic valve, the first throttle valve, and the flowmeter with a flow rate of 17.5 ml/s; so that a 35 ml volume of smoke gas is collected.

6. The method according to claim 1, wherein the precise clean air calibration stage is simultaneously carried out with a cigarette insertion stage, an automatic ignition stage, a first smoke puff stage, and a smoldering/self-sustaining combustion stage, which both last 40 seconds; in the precise clean air calibration stage, a clean air is discharged to outdoor after sequentially passing through the second throttle valve, the sixth two-position two-port electromagnetic valve, the annular working chamber, the third two-position two-port electromagnetic valve with a flow rate of 17.5 ml/s; wherein following operations are performed in order: (1) a tested cigarette sample is inserted into the cigarette holder by an operator within 15 seconds; (2) the ignition coil of the automatic ignition device is energized, shifted 9 mm left to contact the tested cigarette sample and heated up to 380° C. within 5 seconds; (3) a first smoke is sucked for 2 seconds; and (4) the cigarette sample is smoldering/self-sustaining combustion lasting 18 seconds.

7. The method according to claim 1, wherein as soon as the second smoke puff stage with a flow rate of 1,050 ml/min is completed, the ambient air flushing stage with a flow rate of 6,500 ml/min begins; an ambient air is, for 15 seconds, discharged to outdoor after sequentially passing through the third two-position two-port electromagnetic valve, the annular working chamber of the gas sensor array, the fifth two-position two-port electromagnetic valve, the fourth two-position two-port electromagnetic valve; a residual cigarette butt of the cigarette sample is removed and discarded by an operator; the ambient air then is, for 31 seconds, discharged to outdoor after sequentially passing through the first two-position two-port electromagnetic valve, the annular working chamber, the fifth two-position two-port electromagnetic valve and the fourth two-position two-port electromagnetic valve with a flow rate of 6,500 ml/min; at an end of the 31 seconds, a detection period of the cigarette sample ends; if a next cigarette sample needs to be detected, the computer system automatically starts a new detection period and transfers to an early recovery stage; otherwise, the operator clicks an "End Detection" button in a screen drop-down menu to end a detection process.

8. The method according to claim 1, wherein in a data acquisition stage, testing, by the electronic nose instrument, standard samples of tobacco and tobacco products which have been evaluated by an assessor panel and given the sensory quality index scores; a measurement period of a single standard sample is 5 minutes; a steady-state maximum voltage value of a response curve of each gas sensor to the second smoke gas is extracted as a feature component so as to obtain a 16-dimensional voltage response vector for a $p^{th}$ standard sample, wherein a 16-dimensional voltage response vector is $x_p' = (x_{p1}', \ldots, x_{pi}', \ldots, x_{p16}')^T \in R^{16}$; through testing N standard samples, obtaining, by the electronic nose instrument, a standard voltage response dataset $X' \in R^{N \times 16}$ of the gas sensor array and establishing a corresponding relationship between each 16-dimensional voltage response vector is $x_p'$, and scores of the five sensory quality indices including aroma $d_1 \in R^N$, harmony $d_2 \in R^N$, impurity $d_3 \in R^N$, irritation $d_4 \in R^N$ and aftertaste odor $d_5 \in R^N$; wherein 10 standard samples are measured for each brand with 3 grades: A, B and C; if a brand number is n, then N=30n.

9. The method according to claim 1, wherein all feature variables of a standard voltage response dataset X' of the gas sensor array to a standard samples are transformed to a range of [0.0, 6.0] by a positive proportional preprocess; when the steady-state maximum voltage value of a response curve of a gas sensor i to a $p^{th}$ standard sample is $x_{pi}'$, and a value after a proportional transformation is shown in formula (1):

$$x_{pi} = 6 \times \frac{x_{pi}' - \min(X')}{\max(X') - \min(X')} \quad (1)$$

wherein max(X') and min(X') are maximum and minimum values of the standard voltage response dataset X' respectively, $x_{pi}$ is a transformed steady-state maximum voltage value of a response curve of the gas sensor i to the $p^{th}$ standard sample after a proportional transformation; a voltage response vector is thus changed to a 16-dimensional pattern $x_p = (x_{p1}, \ldots, x_{pi}, \ldots, x_{p16})^T \in R^{16}$; and max(X') and min(X') are saved in the computer as basic parameters; after the standard voltage response dataset X' is proportionally transformed, a new data set is called a training set and denoted as X; in a recognition and sensory quality index score estimation stage for an undetermined cigarette pattern x, the max(X) and min(X') are still used to proportionally transform the steady-state maximum voltage value of the response curve $x_{pi}'$ of the gas sensor i by using the formula (1);

wherein each single-output neural network in the cascade modular neural network model is subjected to a learning stage for the training set X, and the recognition and sensory quality index score estimation stage for the undetermined cigarette pattern x.

10. The method according to claim 1, wherein in a learning stage of a first level of the cascade modular neural network model, a training set X is firstly implemented an one-against-one (OAO) decomposition into $C_n^2 = n(n-1)/2$ binary-class training subsets, and then, a n(n-1)/2 binary-class training subsets are learned by the n(n-1)/2 single-output neural networks, one by one, using an error back-propagation algorithm; wherein each single-output neural network is single-hidden-layer in structure, a number of input nodes is m=16, a number of hidden nodes is $s_1=8$ and a number of output nodes is 1; a target output is encoded in {0.0, 3.0}, and an activation functions of all hidden nodes and output nodes are $f(\varphi) = 3(1 + \exp(-\varphi))^{-1}$, wherein the first level is n(n-1)/2 single-output neural networks;

wherein the electronic nose instrument measures all standard samples of two brands $\omega_j$ and $\omega_k$ to obtain a binary-class training subset $X_{jk} = \{X_j, X_k\}$, wherein a number of the all standard samples is $N_{jk} = N_j + N_k = 60$, and the single-output neural network $\overline{\omega}_{jk}$ learns the all standard samples of two brands $\omega_j$ and $\omega_k$ by using a learning factor $\eta_{jk} = 10/N_{jk} = 0.17$;

for a 16-dimensional pattern $x_p = (x_{p1}, \ldots, x_{pi}, \ldots, x_{p16})^T \in R^{16}$, an actual output of a hidden node h in the single-output neural network $\overline{\omega}_{jk}$ is:

$$\xi_{ph}^{(jk)} = f(\varphi_{ph}^{(jk)}) = 3(1 + \exp(-\varphi_{ph}^{(jk)}/3))^{-1} \quad (2)$$

wherein $\varphi_{ph}^{(jk)}$ is a weighted sum of all input components of the 16-dimensional pattern $x_p$ for the hidden node h, or:

$$\varphi_{ph}^{(jk)} = \theta_h^{(jk)} + w_{h1}^{(jk)} x_{p1} + \ldots + w_{hi}^{(jk)} x_{pi} + \ldots + w_{h,16}^{(jk)} x_{p,16} = \sum_{i=0}^{16} w_{hi}^{(jk)} x_{pi} \quad (3)$$

wherein a threshold term is $\theta_h^{(jk)} = w_{h0}^{(jk)}$, and a constant term is $x_{p0} = 6.0$;

for the 16-dimensional pattern $x_p$, an actual output of the single-output neural network $\overline{\omega}_{jk}$ is:

$$y_p^{(jk)} = f(\phi_p^{(jk)}) = 3(1 + \exp(-\phi_p^{(jk)}/3))^{-1} \quad (4)$$

wherein $\phi_p^{(jk)}$ is a weighted sum of outputs of all hidden nodes of the single-output neural network $\overline{\omega}_{jk}$ and shown as:

$$\phi_p^{(jk)} = \theta^{(jk)} + w_1^{(jk)} \xi_{p1}^{(jk)} + \ldots + w_1^{(jk)} \xi_{ph}^{(jk)} + \ldots + w_8^{(jk)} \xi_{p8}^{(jk)} = \sum_{h=0}^{8} w_h^{(jk)} \xi_{ph}^{(jk)} \quad (5)$$

wherein the threshold term is $\theta^{(jk)} = w_0^{(jk)}$, and constant term is $\xi_{p0}^{(jk)} = +3.0$.

11. The method according to claim 1, wherein in a learning stage of a second level of the cascade modular neural network model, a training set X is decomposed into n binary-class training subsets; each binary-class training subset is comprised of all patterns from a single tobacco brand, which respectively fit non-linear relations between responses of gas sensor array and scores of the five sensory quality indices of a corresponding brand; each single-output neural network is single-hidden-layer in structure, with m=16 input nodes and $s_2=8$ hidden nodes; an activation function of all hidden and output nodes is still $f(\varphi) = 3(1 + \exp(-\varphi/3))^{-1}$ with a learning rate $\eta_j = 5/N_j = 0.17$, and a back-propagation learning algorithm is still used, wherein the second level is n×5 single-output neural networks, the all patterns are $N_j = 30$; each of score estimation groups comprises five single-output neural networks and the five sensory quality indices are aroma, harmony, impurity, irritation and aftertaste;

a training subset $X_j$ is composed of $N_j$=30 samples from only the brand $\omega_j$; five single-output neural networks in a score estimation group $\Lambda_j$ fit a non-linear relation between the training subset $X_j$ and the scores of the five sensory quality indices of the brand $\omega_j$, wherein the five sensory quality indices are aroma, harmony, impurity, irritation, and aftertaste; a target output of the training subset $X_j$ are a processed sensory quality index score of the brand $\omega_j$, which is proportionally transformed to a range of [0.15, 2.85];

for a 16-dimensional pattern $x_p$ from the brand $\omega_j$, supposed that a $r^{th}$ sensory quality index score is $d_p^{(jr)'}$, a target output of a $r^{th}$ single-output neural network after proportional transformation is:

$$d_p^{(jr)} = 0.15 + 2.70 \times \frac{d_p^{(jr)'} - \min(d^{(jr)'})}{\max(d^{(jr)'}) - \min(d^{(jr)'})} \quad (6)$$

wherein $d^{(jr)'}=(d_1^{(jr)'}, \ldots, d_p^{(jr)'}, \ldots, d_{30}^{(jr)'})^T$ is a vector of the $r^{th}$ sensory quality index score for all $N_j$=30 standard samples of the brand $\omega_j$, wherein an actual output of a hidden node h of the $r^{th}$ single-output neural network in a score estimation group $\Lambda_j$ is shown in formula (7):

$$\xi_{ph}^{(jr)}=f(\varphi_{ph}^{(jr)})=3(1+\exp(-\varphi_{ph}^{(jr)}/3))^{-1} \quad (7)$$

in the formula (7), $\varphi_{ph}^{(jr)}$ is a weighted sum of all input components of the 16-dimensional pattern $x_p$ for the hidden node h, or:

$$\varphi_{ph}^{(jr)} = \theta_h^{(ph)} + w_{h1}^{(jr)}x_{p1} + \ldots + w_{hi}^{(jr)}x_{pi} + \ldots + w_{h,16}^{(jr)}x_{p,16} = \sum_{i=0}^{16} w_{hi}^{(jr)}x_{pi} \quad (8)$$

wherein a threshold term is $\theta_h^{(jr)}=w_{h0}^{(jr)}$, and a constant term is $x_{p0}$=6.0;

wherein an actual output of the $r^{th}$ single-output neural network in the score estimation group $\Lambda_j$ is shown in formula (9):

$$z_p^{(jr)}=f(\phi_p^{(jr)})=3(1+\exp(-\phi_p^{(jr)}/3))^{-1} \quad (9)$$

in the formula (9), $\phi_p^{(jr)}$ is a weighted sum of real outputs of all hidden nodes of the $r^{th}$ single-output neural network, or:

$$\phi_p^{(jr)} = \theta^{(jr)} + w_1^{(jr)}\zeta_{p1}^{(jr)} + \ldots + w_1^{(jr)}\zeta_{ph}^{(jr)} + \ldots + w_8^{(jr)}\zeta_{p8}^{(jr)} = \sum_{h=0}^{8} w_h^{(jr)}\zeta_{ph}^{(jr)} \quad (10)$$

wherein the threshold term is $\theta^{(jr)}=w_0^{(jr)}$ the constant term is $\xi_{p0}^{(jr)}$=+3.0.

12. The method according to claim 1, wherein a first level of the cascade modular neural network model for recognizing tobacco and tobacco products is that each vote recognition group consists of (n−1) single-output neural networks, representing a specified brand of tobacco and tobacco product, and a maximum number of votes is (n−1); each single-output neural network must join in two of n vote recognition groups, and n(n−1)/2 single-output neural networks constitute n vote recognition groups respectively; a majority vote rule is used for decision-making;

a single-output neural network $\overline{\omega}_{jk}$ must join in a $j^{th}$ vote recognition group $\Omega_j$ and a $k^{th}$ vote recognition group $\Omega_k$ for vote; in the $j^{th}$ vote recognition group, if an actual output $y^{(jk)}$ of the single-output neural network $\overline{\omega}_{jk}$ satisfies $y^{(jk)}$>1.5, a probability of estimating an undetermined cigarette pattern x to belong to the brand $\omega_j$ obtains 1 vote; in the $k^{th}$ vote recognition group, if the actual output $y^{(jk)}$<1.5, a probability of belonging to the brand $\omega_k$ is given 1 vote;

a decision rule is that the undetermined cigarette pattern x belongs to a brand represented by a vote recognition group with a highest number of votes in the n vote recognition groups; if two or more vote recognition groups have n equal and highest vote number, a decision-making is that the undetermined cigarette pattern x does not belong to any existing brand;

a second level of the cascade modular neural network model which is used for the sensory quality index score estimation of tobacco and tobacco products is that each score estimation group consists of five single-output neural networks, which is responsible for performing the score estimation of the five sensory quality indices of a corresponding brand, wherein the five sensory quality indices are aroma, harmony, impurity, irritation and aftertaste; n×5 single-output neural networks are divided into n score estimation groups, corresponding to n vote recognition groups with an one-against-one relationship;

in a score estimation stage of the five sensory quality indices of the undetermined cigarette sample x, on a premise that the vote recognition group $\Omega_j$ in the first level of the cascade modular neural network model gets a largest number of votes, a score estimation group $\Lambda_j$ in a second level, representing the brand $\omega_j$, takes part in an estimation alone, while another score estimation groups do not need to;

suppose an actual output of the $r^{th}$ single-output neural network in the score estimation group $\Lambda_j$ is $z^{(jr)}$, a estimated score of the $r^{th}$ sensory quality index of the brand $\omega_j$ is:

$$z^{(jr)'} = (z^{(jr)} - 0.15) \times \frac{\max(d^{(jr)'}) - \min(d^{(jr)'})}{2.70} + \min(d^{(jr)'}) \quad (11)$$

13. The method according to claim 1, wherein if a new brand is added to n existing brands, only n single-output neural networks need to be added to a first level of a cascade modular neural network model and learnt; a number of the first level of the cascade modular neural network model is thus increased from an existing n(n−1)/2 to a new n(n+1)/2; for an added brand $\omega_{n+1}$, newly added and learned single-output neural networks are $\overline{\omega}_{(n+1)}, \ldots, \overline{\omega}_{(n+1)}, \ldots, \overline{\omega}_{(n+1)}$;

correspondingly, to estimate five sensory quality index scores for a newly added brand, five new single-output neural networks are added to a second level of the cascade modular neural network model and learnt, and therefore a number of single-output neural networks is varied from an existing n×5 to (n+1)×5; a fake brand or an existing same brand produced by another manufacturer is regarded as a separate brand for a recognition and the sensory quality index score estimation.

14. The method according to claim 1, wherein the electronic nose instrument performs detection, recognition and sense quality index score estimation operations for cigarette samples by following stages:
- (1), a power-on stage: during the power-on stage, the electronic nose instrument is preheated for 30 minutes, and an ambient air is discharged to outdoor after sequentially passing through the first two-position two-port electromagnetic valve, the annular working chamber of the gas sensor array, the fifth two-position two-port electromagnetic valve, and the fourth two-position two-port electromagnetic valve with a flow rate of 6,500 ml/min; so that a temperature of the thermostatic room is raised from a room temperature to a constant temperature of 55±0.1° C.;
- (2), the smoke sampling stage: when an operator clicks a "Start detection" button in a screen drop-down menu, the electronic nose instrument enters a smoke sampling period lasting 5 minutes, and the computer automatically generates a text file named "xxx" in a designated folder to record a response data of a gas sensor array to a smoke gas;
- (3), the early recovery stage: within 0.00-210.00 s time interval of a smoke sampling period, the ambient air is discharged to outdoor after sequentially passing through the first two-position two-port electromagnetic valve, the annular working chamber, the fifth two-position two-port electromagnetic valve and the fourth two-position two-port electromagnetic valve with the flow rate of 6,500 ml/min; under a flushing operation of the ambient air with the flow rate of 6,500 ml/min, smoke molecules adhered onto surfaces of sensitive films of gas sensors and inner walls of pipelines are flushed away tentatively, so that the gas sensor array returns to a reference state preliminarily for 210 s;
- (4), the precise clean air calibration stage: within 210.00-250.00 s time interval of the smoke sampling period, two following stages are carried out simultaneously: (a) the precise clean air calibration stage, and (b) a cigarette insertion stage, an automatic ignition stage, a first smoke puff stage, and a smoldering/self-sustaining combustion stage; which last 40 s;
- (4a), the precise clean air calibration stage: a clean air flows are, for 40 s, discharged to outdoor after sequentially passing through the second throttle valve, the sixth two-position two-port electromagnetic valve, the annular working chamber of the gas sensor array, and the third two-position two-port electromagnetic valve with a flow rate of 17.5 ml/s; so that the gas sensor array returns to the reference state accurately;
- (4b.1), the cigarette insertion stage: within 210.00-225.00 s time interval of the smoke sampling period, which is first 15 s time slot of the precise clean air calibration stage, a screen displays a word "Cigarette insertion", the operator inserts a filter end of a tested cigarette sample into the cigarette holder, at an insertion depth of 9.0±0.5 mm;
- (4b.2), the automatic ignition stage: within 225.00-231.00 s time interval of the smoke sampling period, which is 15.00-21.00 s time slot of the precise clean air calibration stage, the ignition coil is energized; meanwhile, the cigarette igniter head moves 9 mm to left so as to contact and ignite the tested cigarette sample for 6 s; in 231.00-269.00 s of the smoke sampling period, the electromagnetic coil is powered, and the ignition coil is powered off and returned to a reference position for 38 s, including a later is of the first smoke puff stage, 18 s of the smoldering/self-sustaining combustion stage, 2 s of the balance stage, 2 s of the second smoke puff stage, and 15 s of a residual cigarette butt removal stage;
- (4b.3), the first smoke puff stage: within 230.00-232.00 s time interval of the smoke sampling period, which is 20.00-22.00 s time slot of the precise clean air calibration stage, under a suction action of the miniature vacuum pump, the smoke gas is, for 2 s, directly discharged to outdoor after sequentially passing through the second two-position two-port electromagnetic valve, the first throttle valve and the flowmeter with the flow rate of 17.5 ml/s;
- (4b.4), the smoldering/self-sustaining combustion stage: within 232.00-250.00 s time interval of the smoke sampling period, which is 22.00-40.00 s time slot of the precise clean air calibration stage, the second two-position two-port electromagnetic valve is disconnected, so that the tested cigarette sample enters the smoldering/self-sustaining combustion stage, which lasts 18 s;
- (5), the balance stage: within 250.00-252.00 s time interval of the smoke sampling period, all two-position two-port electromagnetic valves are disconnected; so that no gas flows in the annular working chamber of the gas sensor array and the tested cigarette sample is still in the smoldering/self-sustaining combustion stage for 2 s;
- (6), the second smoke puff stage: within 252.00-254.00 s time interval of the smoke sampling period, the first two-position two-port electromagnetic valve and the fifth two-position two-port electromagnetic valve are connected, and the second two-position two-port electromagnetic valve, the third two-position two-port electromagnetic valve, the fourth two-position two-port electromagnetic valve, the sixth two-position two-port electromagnetic valve are disconnected; cigarette smoke is, for 2 s, discharged to outdoor after sequentially passing through the first two-position two-port electromagnetic valve, the annular working chamber of the gas sensor array, the fifth two-position two-port electromagnetic valve, the first throttle valve and the flowmeter with the flow rate of 17.5 ml/s, so that a 35 ml volume of smoke gas is collected;
- (7), the ambient air flushing stage: within 254.00-300.00 s time interval of the smoke sampling period, an indoor ambient air flows through the annular working chamber of the gas sensor array with the flow rate of 6,500 ml/min; the smoke molecules adhered to the surfaces of sensitive films of gas sensors and the inner walls of pipelines are roughly flushed away, so that the gas sensor array enters the early recovery stage, which comprises following two stages: a residual cigarette butt removal stage and a post removal stage;
- (7.1), the residual cigarette butt removal stage: within 254.00-269.00 s time interval of the smoke sampling period, the operator takes out and discards the residual cigarette butt within 15 s; during the 15 s duration, the third two-position two-port electromagnetic valve, the fourth two-position two-port electromagnetic valve and the fifth two-position two-port electromagnetic valve are turned on, and the first two-position two-port electromagnetic valve, the second two-position two-port electromagnetic valve and the sixth two-position two-port electromagnetic valve are switched off, and the ambient air is, for 15 s, discharged to outdoor after sequentially passing through the third two-position two-port electromagnetic valve, the annular working chamber of the gas sensor array, the fifth two-position two-port electromagnetic valve and the fourth two-position two-port electromagnetic valve at the rate of 6,500 ml/min;

(7.2), the post removal stage: within 269.00-300.00 s time interval of the smoke sampling period, the first two-position two-port electromagnetic valve, the fourth two-position two-port electromagnetic valve and the fifth two-position two-port electromagnetic valve are connected; and the second two-position two-port electromagnetic valve, the third two-position two-port electromagnetic valve and the sixth two-position two-port electromagnetic valve are disconnected; the ambient air is, for 31 s, discharged to outdoor after sequentially passing through the first two-position two-port electromagnetic valve, the annular working chamber of the gas sensor array, the fifth two-position two-port electromagnetic valve and the fourth two-position two-port electromagnetic valve at the flow rate of 6,500 ml/min; wherein positions of the first to sixth two position two port electromagnetic valves and the flow rate of ambient air are exactly same as the early recovery stage of the gas sensor array;

(8), a data recording stage: from a time point of 250.00 s time interval in the smoke sampling period, which is from the beginning of the balance stage, the computer saves voltage responses of 16 gas sensors in a "xxx" text file through the 16-channel 16-bit high-precision data acquisition card until a time point of 290.00 s, including the second smoke puff stage, the residual cigarette butt removal stage and the post removal stage; the duration of the data recording stage is 40 s after the residual cigarette butt removal stage;

(9), a feature extraction stage: in the smoke sampling period, the computer control and data analysis system extracts, for 40 s, the steady-state maximum voltage value of the response curve of each gas sensor from the "xxx" data recording file as a response component, which represents a response to the second smoke gas, so that a tobacco and tobacco product sample is transformed into a 16-dimensional measurement pattern, and stored in a data set file of tobacco and tobacco product samples in the hard disk;

(10), a recognition and sensory quality index score estimation stage: within 290.00-300.00 s time interval of the smoke sampling period, or 10 s after an end of the data recording stage, a first level of the cascade modular neural network model, which is n vote recognition groups, determines a brand, origin and authenticity of a tested cigarette sample according to a majority vote rule; and a score estimation group in a second level of the cascade modular neural network model corresponding to a winning vote recognition group performs the score estimation of the five sensory quality indices, which are aroma, harmony, impurity, irritation and aftertaste, and the recognition and score estimation results are displayed on a monitor;

by repeating the stages (2)-(10), the electronic nose instrument realizes smoke detection, recognition and sensory quality index score estimation for a plurality of tobacco and tobacco product samples; wherein a complete test period for a tobacco and tobacco product sample takes 300 s.

* * * * *